United States Patent [19]

Palva et al.

[11] Patent Number: 5,242,821
[45] Date of Patent: Sep. 7, 1993

[54] LACTOCOCCUS PROMOTER AND SIGNAL SEQUENCES FOR EXPRESSION IN BACTERIA

[75] Inventors: Ilkka Palva; Mervi Sibakov, both of Helsinki, Finland

[73] Assignee: Valio, Finnish Co-Operative Dairies' Association, Helsinki, Finland

[21] Appl. No.: 377,450

[22] Filed: Jul. 10, 1989

[51] Int. Cl.$^5$ .................. C12N 1/21; C12N 15/74
[52] U.S. Cl. .................. 435/252.3; 435/172.3; 435/252.31; 435/320.1
[58] Field of Search ............. 435/69.1, 71.2, 252.3, 435/172.3, 252.31, 320.1, 252.9; 935/41; 536/27

[56] References Cited

U.S. PATENT DOCUMENTS

| | | | |
|---|---|---|---|
| 4,725,535 | 2/1988 | Sonenshein et al. | 435/6 |
| 4,963,495 | 10/1990 | Chang et al. | 435/320.1 |
| 5,037,760 | 8/1991 | Smith et al. | 435/69.1 |

FOREIGN PATENT DOCUMENTS

0157441 9/1985 European Pat. Off.
62-069989 3/1987 Japan.

OTHER PUBLICATIONS

Hayes, F. et al., *Applied and Environmental Microbiology* 56:202–209 (1990).
Teixeria, A. V. et al., *Gene* 81: 159–163 (1989).
Forster, J. W., et al., *Mol. Gen. Genet.* 211: 531–537 (1988).
Fujita, Y. et al., *Proc. Natl. Acad. Sci. USA* 84: 4524–4528 (1987).
Dhaese, P. et al., *Gene* 32:181–194 (1984).
de Vos, *Neth. Milk Dairy J.* 40:141–154 (1986).
de Vos, *FEMS Microbiol. Rev.* 46:281–295 (1987).
Kok et al., *Applied Environmental Microbiol.* 50: 94–101 (1985).
van der Vossen et al., *Applied Environmental Microbiol.* 50:540–542 (1985).
van der Vossen et al., *Applied Environmental Microbiol.* 53:2452–2457 (1987).
Kok et al., *Applied Environmental Microbiol.* 54:239–244 (1988).
van de Guchte et al., *Applied Environmental Microbiol.* 55:224–228 (1989).
Simons et al., *J. Dairy Sci.* 71 (Supp 1):Abstr. D64 (1988).
Vos et al., *J. Dairy Sci.* 71 (Supp 1):Abst. D65 (1988).
Kondo, *J. Dairy Sci.* 71 (Supp 1):Abstr. D125 (1988).
de Vos, *J. Dairy Sci.* 71 (Supp 1):Abstr. D127 (1988).
McKnight et al., *J. Dairy Sci.* 71 (Supp 1):Abstr. D108 (1988).
Smith et al., *J. Bacteriol.* 169(7):3321–3328 (1987).
Achen et al. (1986), *Gene*, vol. 45, pp. 45–49.
von Wright et al. (1987) Applied & Environmental Microbiology, vol. 53, No. 7, pp. 1584–1588.

*Primary Examiner*—Richard A. Schwartz
*Assistant Examiner*—J. Le Guyader
*Attorney, Agent, or Firm*—Sterne, Kessler, Goldstein & Fox

[57] ABSTRACT

DNA sequences, derived from *Lactococcus lactis* subsp. lactis, are useful as promoters nd promoter/secretion promoting signals for heterologous or homologous expression in Gram-positive bacteria. In another aspect, the invention relates to vectors, such as plasmids, comprising the sequences of the present invention, and to host cells transformed with such vectors. Yet additional aspects of the present invention are related to methods for producing desired heterologous or homologous peptides or proteins employing the sequences, vectors, or transformed hosts of the invention. By means of the invention, greatly improved heterologous and homologous expression and secretion may be achieved in *E. coli* and in Gram-positive bacteria such as *B. subtilis*, Lactococci and Lactobacillus.

13 Claims, 20 Drawing Sheets

EcoRI PvuII BglII

5'        GAATTCAGCTGAGATCTTGCA 3'
3' ACGTCTTAAGTCGACTCTAGA        5'

FIG. 1

```
        490        480        470        460        450        440
   CGAGCTCGTA CCCAGCTGAT TGATTAAGCC GATGAACTCA TCAGCGATAA TCAAATGCCC 430        420        410        400        390        380
   GTTGAAGAAA TAGGTAACCA CTCAGTGATC CCTTCAATAA TACCTAAAAT AATGGCACGA 370        360        350        340        330        320
   ATAAAATCCA TATTTTGCTC CTAGAAAATT TCAGTAAAAA GACTGATTTT TATCGACTGA 310        300        290        280        270        260
   CAGAGCAGTC TTACTTTCTA AGTATATCAT ATAAAGGGGA ATGAATAAAC TTACAAAAAA 250        240        230        220        210        200
   ACTGATTACT TGTAACTAAT TTTACATTCT CATCCTTGAC ATCATTCCAA AATTGCGCTA 190        180        170        160        150        140
   GAATTACAAC TAACACATCG ATAGAGGTCG CAACTGATAT GAATCTACGC CGAGTTGGAG 130        120        110        100         90         80
   CACAACAAAG ACGCGTATTA GAGGGGGAGA AGTTGCCGAA AGAATTTTGA CGCTCAGCAA
         ┌─── SEQUENCE FROM THE VECTOR
         │  70         60         50         40         30         20
   AGGGGATCCT CTAGAGTCAC TTTCGCCACG TTGGCGGAAA CAAACCTGAC AACATGAACT
   ‾‾‾‾‾‾‾‾‾‾
         10
   ATGAAGAGGT GACGTCATG
```

FIG. 13

PROMOTER PROBE VECTOR pKTH 1750

1  T G C A  2

3  T G C A  4

```
       10        20        30        40        50        60
        ·         ·         ·         ·         ·         ·
  1  AAAAAGAAACACCCGAAAGCATTGCCATAGGTACTCTTATCAGTAATCTGAAAATAAAAA

61  TGGACTCAGGCTAGAAAAATAAAGGCTTTTATGAAAGAAAGACTTGCATTTGTTGTTGAA

121  AAATGCTAAAATACATAAGTCCGACTTTTTAGATATATTTAAATTTGTATTTATATCTTT

181  CGGGAAATTTTTAAGGAGGTACTTTTGCTTGGCAAAAGATGATGTAATTGAAGTAGACGG

241  CAAAGTCGTTGACACCATGCCGAATGCGATGTTCACTGTTGAACTCGAAAATGGTCACCA

301  AGTCTTGGCGACGATTTCAGGAAAAATTCGTAAGAATTATATCCGTATCTTGCCTGGAGA

361  CAAGGTTCAAGTTGAACTCTCACCATACGATTTGACACGCGGACGAATTACTTACCGATT

421  TAAGTAATCCGGACATTCATTGAGTGCATGATGCACAGTAACCATAGAAAGGAAGACACA

481  ATGAAAGTAAGACCATCAGTTAAACCAATCTGCGAATACTGTAAAGTTATTCGTCGTAAC

541  GGTCGTGTAATGGTAATTTGCCCTGCCAATCCAAAACACAAACAACGTCAGGGATAGAAA

601  GGAAATAGCAAAAATATGGCTCGTTTTGCTGGAGTTGATATTCCAAACGAAAAACGCATT

661  GTTATTTCATTAACATACGTATTCGGTGTTGGACTTCAAACATCTAAGAAAGTACTTGCA

721  GCTGCAGGTGTTTCAGAAGATATCCGTACTAAAGATTTGACATCAGATCTTGC
                                                        └─► VECTOR
```

FIG. 9

```
        10        20        30        40        50        60
         ○         ○         ○         ○         ○         ○
  1  GCGCAACTAAAGCCCATGCCAAAGATAAACTTCCCATTCTCTTGATTCATGGAAGCAAAG

61  ATACATATGTTCCAACTTCAATGGTCTATGAGAACTACAAATCAGTCAAGCTCGGAACGC

121  CCAAAGAAATGTTAGTTGTTAAAAACGCTCGTCACGCTCGGTCTTTCCAAACAAATCCCA

181  CACTCTATCATCAAACAATTTCAAAATTTATGAAGACTTATAATCCGTAATTTATTGACT

241  TTTATATCAGTGATTTATGAGTTTTTTCTTGACAGAAGATGGCGAAAAATGGTATTATAT
             (•)•
301  CTAGGTACTGTTTTGCGGTGGTGGCGGAATTGGCAGACGCGCAGGATTAAGGATCTTGC
                                                    └──→ VECTOR
```

FIG. 10

```
        10        20        30        40        50        60
         ○         ○         ○         ○         ○         ○
  1  TTGATAGAGGAATAGTATTTTATCTATTCCTTTTTTTGCTGACAAAAACCTAATTTATTT

61  TAAATTTTTGCATGTAATGAGTTTATTCTTGACAACTTTTGGGAAACTTGGTATACTAAT
           (•)
121  ATAGTCGTTTAAGAGAAACGCAGGCGTGGCTCAACTGGATAGAGTACCTGACTACGAATC
                                       •
181  AAAAGGCGGTTGTAGGTTCGAATCCTACCGCTTGCATAAATAAAATATGACGAAAGTCAT

241  TTTTTTATTTGAAAGCTGATCTTGC
                └──→ VECTOR
```

FIG. 11

```
           10        20        30        40        50        60
            ö         ö         ö         ö         ö         ö
  1  AAGTTGAATCACTGACAGCCATTCAAAATTACTGACAGCTTCGTCAGTAAAAATGATGAA
                                                                    SEQUENCE
 61  TGTTTAATAAAAAATTATAAGAGAAAAATCACTGACAATCGGTGATTCTTTAAGTTTTTT    FROM
                                                              ↓     THE VECTOR
121  CTGTCCTATGTTAAAATAGAGGAATATAGGAGTAATATTATGAATTTTGTCCGGGGATCC
                                                              - - - →
181  TCTAGAGTCACTTTCGCCACGTTGGCGGAAACAAACCTGACAACATGAACTATGAAGAGG

241  TGACGTCATGAAA
```

FIG. 12

```
         10        20        30        40        50        60
         ȯ         ȯ         ȯ         ȯ         ȯ         ȯ
AATTCCAAAAATTTGTTATAATCGATATGTGAATTTTAACACAAAAGGAGTAACTATGAA
```

AsnSerLysAsnLeuLeu---SerIleCysGluPhe---HisLysArgSerAsnTyrGlu
IleProLysIleCysTyrAsnArgTyrValAsnPheAsnThrLysGlyValThrMETLys
PheGlnLysPheValIleIleAspMET---IleLeuThrGlnLysGlu---Leu---Lys

```
         70        80        90       100       110       120
         ȯ         ȯ         ȯ         ȯ         ȯ         ȯ
AATTTGGACAAAACTGGGCTTGCTCTCGCTTGTAGGCCTCACTTTAACAGCTTGTGGAAG
```

AsnLeuAspLysThrGlyLeuAlaLeuAlaCysArgProHisPheAsnSerLeuTrpLys
IleTrpThrLysLeuGlyLeuLeuSerLeuValGlyLeuThrLeuThrAlaCysGlySer
PheGlyGlnAsnTrpAlaCysSerArgLeu---AlaSerLeu---GlnLeuValGluAla

```
        130       140       150       160       170       180
         ȯ         ȯ         ȯ         ȯ         ȯ         ȯ
CAACACAAAGACAGCTAAAGAACAATCGAGTTCGTCTCAAAAAGTTGAAACTTCTGCTGG
```

GlnHisLysAspSer---ArgThrIleGluPheValSerLysSer---AsnPheCysTrp
AsnThrLysThrAlaLysGluGlnSerSerSerGlnLysValGluThrSerAlaGly
ThrGlnArgGlnLeuLysAsnAsnArgValArgLeuLysLysLeuLysLeuLeuLeuVal

FIG. 14

```
     190       200       210       220       230       240
      ö         ö         ö         ö         ö         ö
TGCAAGTAAATCAAACACTTATGCAGACCCTTCAACATTAAGTGATAAATATGATGTTAT

CysLys---IleLysHisLeuCysArgProPheAsnIleLys------Ile---CysTyr
AlaSerLysSerAsnThrTyrAlaAspProSerThrLeuSerAspLysTyrAspValIle
GlnValAsnGlnThrLeuMETGlnThrLeuGlnHis---ValIleAsnMETMETLeuLeu 250       260       270       280       290       300
      ö         ö         ö         ö         ö         ö
TATTGTCGGTTCAGGCGGAGCTGGAATGACAGCAGCAATCGAAGCGAAAGATGCTGGAAT

TyrCysArgPheArgArgSerTrpAsnAspSerSerAsnArgSerGluArgCysTrpAsn
IleValGlySerGlyGlyAlaGlyMETThrAlaAlaIleGluAlaLysAspAlaGlyIle
LeuSerValGlnAlaGluLeuGlu---GlnGlnGlnSerLysArgLysMETLeuGluPhe 310       320
      ö         ö
```

TCCCCCAGAAACGCTGGTGAAA
┌── N-terminus of TEM-bla
↓
SerProArgAsnAlaGlyGlu
 ProProGluThrLeuValLys
  ProGlnLysArgTrp---

FIG. 14 (cont.)

```
        10        20        30        40        50        60
         o         o         o         o         o         o
AAATTTTCATTTGCTTCCGATTTACTGACTTAAAAGTTAAAGATATAGTAAATTATAAAA
```

LysPheSerPheAlaSerAspLeuLeuThr---LysLeuLysIle------IleIleLys
 AsnPheHisLeuLeuProIleTyr---LeuLysSer---ArgTyrSerLysLeu---Asn
  IlePheIleCysPheArgPheThrAspLeuLysValLysAspIleValAsnTyrLysIle

```
        70        80        90       100       110       120
         o         o         o         o         o         o
TAAAAATGTATTTTTTGAAATCAAAATTACATTTTTTGCTTGCTTAAATGAAACTAAACA
```

---LysCysIlePhe---AsnGlnAsnTyrIlePheCysLeuLeuLys---Asn---Thr
 LysAsnValPhePheGluIleLysIleThrPhePheAlaCysLeuAsnGluThrLysHis
  Lys<u>MET</u>TyrPheLeuLysSerLysLeuHisPheLeuLeuAla---<u>MET</u>LysLeuAsn<u>MET</u>

```
       130       140       150       160       170       180
         o         o         o         o         o         o
TGTTATACTCCTAGTATTATGAAAAAAATTTTAATTACTACGACTCTTGCACTTGCTCTT
```

CysTyrThrProSerIle<u>MET</u>LysLysIleLeuIleThrThrThrLeuAlaLeuAlaLeu
 ValIleLeuLeuValLeu---LysLysPhe---LeuLeuArgLeuLeuHisLeuLeuPhe
  LeuTyrSer---TyrTyrGluLysAsnPheAsnTyrTyrAspSerCysThrCysSerSer

FIG. 15

```
        190       200       210       220       230       240
         ȯ         ȯ         ȯ         ȯ         ȯ         ȯ
CTCTCGTTAGGAGCTTGCTCTAAAAAATCAGACAGTAAAGCCAAAGCCAGTTCATCTGTT

LeuSerLeuGlyAlaCysSerLysLysSerAspSerLysAlaLysAlaSerSerSerVal
 SerArg---GluLeuAlaLeuLysAsnGlnThrValLysProLysProValHisLeuPhe
  LeuValArgSerLeuLeu---LysIleArgGln---SerGlnSerGlnPheIleCysPhe 250       260       270       280       290       300
         ȯ         ȯ         ȯ         ȯ         ȯ         ȯ
TCATCAACGGCTATCTCCTCTTCAAGTTCAACATCTTCTTCAAAAAAAGTTGAAAATACT

SerSerThrAlaIleSerSerSerSerSerThrSerSerSerLysLysValGluAsnThr
 HisGlnArgLeuSerProLeuGlnValGlnHisLeuLeuGlnLysLysLeuLysIleLeu
  IleAsnGlyTyrLeuLeuPheLysPheAsnIlePhePheLysLysSer---LysTyrSer 310       320       330       340       350
         ȯ         ȯ         ȯ         ȯ         ȯ
CAAGAAAATATTAGCTCTAGCTTTCAAATGACTGTAGAGATTCCCCCAGAAA

N-terminus of TEM-bla─┐
                                                ↓
GlnGluAsnIleSerSerSerPheGlnMETThrValGluIleProProGlu
 LysLysIleLeuAlaLeuAlaPheLys---Leu---ArgPheProGlnLys
  ArgLysTyr---Leu---LeuSerAsnAspCysArgAspSerProArg
```

FIG. 15 (cont.)

```
          10        20        30        40        50        60
          ö         ö         ö         ö         ö         ö
       GATAGTCTTTTCCTTCATTCTTTTCGCCAAAAACTGGAATATGATTCATAAAAATTTTCC

AspSerLeuPheLeuHisSerPheArgGlnLysLeuGluTyrAspSer---LysPheSer
         IleValPheSerPheIleLeuPheAlaLysAsnTrpAsnMETIleHisLysAsnPhePro
           ---SerPheProSerPhePheSerProLysThrGlyIle---PheIleLysIlePhePro 70        80        90       100       110       120
          ö         ö         ö         ö         ö         ö
       CCCAAAATTGATTTACATGATAAAAGTTAAATATTTCATTATGTAAAAACCGCTTACAAA

ProLysIleAspLeuHisAspLysSer---IlePheHisTyrValLysThrAlaTyrLys
         ProLysLeuIleTyrMETIleLysValLysTyrPheIleMET---LysProLeuThrLys
           GlnAsn---PheThr-------LysLeuAsnIleSerLeuCysLysAsnArgLeuGlnLys

┌─► 5' end of mRNA
         130       140       150       160       170  │  180
          ö         ö         ö         ö         ö   •  ö
       AATTTATTACTACTATTGTATCAAAATTCTGTCAAATTTGATAAAATAAGGTACGAGTAA AsnLeuLeuLeuLeuLeuTyrGlnAsnSerValLysPheAspLysIleArgTyrGlu---
         IleTyrTyrTyrTyrCysIleLysIleLeuSerAsnLeuIleLys---GlyThrSerLys
           PheIleThrThrIleValSerLysPheCysGlnIle------AsnLysValArgValArg 190       200       210       220
           ö         ö         ö         ö
       GAAGAACTTATACAATGATCATATTGAAAAAATATAATTCAA
                                      ═══════════── OVERLAPPING WITH THE BEGINNING
       GluGluLeuIleGln---SerTyr---LysAsnIleIleGln  OF THE NEXT PAGE
         LysAsnLeuTyrAsnAspHisIleGluLysIle---Phe
           ArgThrTyrThrMETIleIleLeuLysLysTyrAsnSer
```

FIG. 16

```
         10        20        30        40        50        60
          ȯ         ȯ         ȯ         ȯ         ȯ         ȯ
ATATAATTCAAGAAGAGAGATGTTATAAGAGGTATTTTTGCATTGGGCAAAAAGCGATGT

Ile---PheLysLysArgAspValIleArgGlyIlePheAlaLeuGlyLysLysArgCys
TyrAsnSerArgArgGluMETLeu---GluValPheLeuHisTrpAlaLysSerAspVal
IleIleGlnGluGluArgCysTyrLysArgTyrPheCysIleGlyGlnLysAlaMET 70        80        90       100       110       120
          ȯ         ȯ         ȯ         ȯ         ȯ         ȯ
GAAATCACATGGCTTTCGAACCTAAAAGAGATGGGTTTGAAACGTATTACTGAAGGGAAC

GluIleThrTrpLeuSerAsnLeuLysGluMETGlyLeuLysArgIleThrGluGlyAsn
LysSerHisGlyPheArgThr---LysArgTrpVal---AsnValLeuLeuLysGlyThr
AsnHisMETAlaPheGluProLysArgAspGlyPheGluThrTyrTyr---ArgGluPro 130       140       150       160       170       180
          ȯ         ȯ         ȯ         ȯ         ȯ         ȯ
CTAGAATAGTGAAAAAAATTAACTTAAGTAAGCTTATTATTATTGCACTCATTATCATTA

LeuGlu------LysLysLeuThr---ValSerLeuLeuLeuLeuHisSerLeuSerLeu
---AsnSerGluLysAsn---LeuLys---AlaTyrTyrTyrCysThrHisTyrHisTyr
ArgIleValLysLysIleAsnLeuSerLysLeuIleIleIleAlaLeuIleIleIleIle 190       200       210       220       230       240
          ȯ         ȯ         ȯ         ȯ         ȯ         ȯ
TTGCAGCGATGTCAGCAATTTTTATTTCAGCCAAAAATTTTAAGTCCAATAAAAATCCGT

LeuGlnArgCysGlnGlnPheLeuPheGlnProLysIleLeuSerProIleLysIleArg
CysSerAspValSerAsnPheTyrPheSerGlnLysPhe---ValGln---LysSerVal
AlaAlaMETSerAlaIlePheIleSerAlaLysAsnPheLysSerAsnLysAsnProSer 250       260       270       280       290       300
          ȯ         ȯ         ȯ         ȯ         ȯ         ȯ
CAGCAATGACCCAAACAATTAATGATGGGACGAGTTTTGTTGACCGAGTTCTTGTTGCAC

GlnGln---ProLysGlnLeuMETMETGlyArgValLeuLeuThrGluPheLeuLeuHis
SerAsnAspProAsnAsn------TrpAspGluPheCys---ProSerSerCysCysThr
AlaMETThrGlnThrIleAsnAspGlyThrSerPheValAspArgValLeuValAlaPro 310       320       330       340       350       360
          ȯ         ȯ         ȯ         ȯ         ȯ         ȯ
CAATCCATTTTGTACAAGACAAAGCAAATGAGCTTTCAAACTTGATAATTCCCCCAGAAA

GlnSerIleLeuTyrLysThrLysGlnMETSerPheGlnThr------PheProGlnLys
AsnProPheCysThrArgGlnSerLys---AlaPheLysLeuAspAsnSerProArgAsn
IleHisPheValGlnAspLysAlaAsnGluLeuSerAsnLeuIleIleProProGluThr
                                                           ↑
CGCTGGT                                          N-terminus of TEM-bla ArgTrp
AlaGly
Leu
```

FIG. 16 (cont.)

```
         10        20        30        40        50        60
         o         o         o         o         o         o
ATCATATTCTTTCCCTAAAGACAGGAAGCTGCTCATTCTCTAAGAATTGAGCATTTTCCC
```

IleIlePhePhePro---ArgGlnGluAlaAlaHisSerLeuArgIleGluHisPhePro
SerTyrSerPheProLysAspArgLysLeuLeuIleLeu---GluLeuSerIlePhePro
HisIleLeuSerLeuLysThrGlySerCysSerPheSerLysAsn---AlaPheSerArg

```
         70        80        90       100       110       120
         o         o         o         o         o         o
GTATTATTTACAAAACATTTACATAAGAACGCTGTCATCAAGCGACCTTTGAGGGGGCAT
```

ValLeuPheThrLysHisLeuHisLysAsnAlaValIleLysArgProLeuArgGlyHis
TyrTyrLeuGlnAsnIleTyrIleArgThrLeuSerSerSerAspLeu---GlyGlyIle
IleIleTyrLysThrPheThr---GluArgCysHisGlnAlaThrPheGluGlyAlaLeu

⌐→ 5' end of mRNA
```
        130       140       150       160       170       180
         o         o         o         o         o         o
TATGTTATAATTAAGCTATGAAGAAGAAAATTTTTATTGCTTTGATGGCCAGTGTAAGTT
```

TyrValIleIleLysLeu---ArgArgLysPheLeuLeuLeu---TrpProVal---Val
METLeu---LeuSerTyrGluGluGluAsnPheTyrCysPheAspGlyGlnCysLysPhe
CysTyrAsn---AlaMETLysLysLysIlePheIleAlaLeuMETAlaSerValSerLeu

```
        190       200       210       220       230       240
         o         o         o         o         o         o
TATTTACATTGGCAGCTTGTGGTTCTGGAAATAAACAGGTCACAGCTATTCCCCCAGAAA
```

TyrLeuHisTrpGlnLeuValValLeuGluIleAsnArgSerGlnLeuPheProGlnLys
IleTyrIleGlySerLeuTrpPheTrpLys---ThrGlyHisSerTyrSerProArgAsn
PheThrLeuAlaAlaCysGlySerGlyAsnLysGlnValThrAlaIleProProGluThr
                                                     N-terminus of TEM-bla

CGCTGGT

ArgTrp
 AlaGly

FIG. 17

Cla I

A  5'   AATTTCCATCGATTTCACGTTGGGCAAGATGACTTACG   3'

Xba I

B  5'   TCCATTTCTAGATATAATACCATTTTTCGCCATCTT   3'

Pvu II

C  5'   TCCTTTCTCAGCTGATCTAGAGTAAGAAGAACTTATACAATGAT   3'

Pvu II  Bgl II

D  5'   TTTTCTTCAGCTGCTAGATCTGCAAGCAGCAGATTACGCGCAGAA   3'

FIG. 18

```
        10        20        30        40        50
         o         o         o         o         o
  1  AAGCGCGTGATTTAGTGCATGATTTAACTTTACAAGGAGAAGATTTAATT

51  AAAATTTTAGCGATTTTGACTAATTCTTATCGATTGTATTTGCAAGTCAA

101  ACTTTTTCAAGAAAAGGGTTGGCAAGAAAATCAACAGGTTTCATATCTGA

151  AGATGCACCCATATCCAGTGAAATTGGCTAATCAATTGGTCCGAAGATTG

201  CAAGTGAGTTCTTTAAAAAAAGGACTTGCTGATTTAATTCAACTCGATTT

251  TGCGATAAAAACGAGTGCAGCTGAAAAAGCTTATCTTTTTGATATCCTAT

301  TAATCAAGTTGACCTTGAAAAAAAACTGAAAATCTGTTATCATAAATAAT

351  GGACATTTTATAATGATGATGATGAAGAGGTAAAAATGGCCGACATTTAA

401  ATTTACGCCTAAAGATATCTAAATGAAGCAGACTTCTCTCCAAAGATGCG

451  TGGTTACGATAAAGAAGAAGTCGATGAACTCCTTGATGACGTTATTGCTG

501  ATTATGAAACTTATCAGACAGAAACATTGCGTCTCCAAGAAGAAAATGAG

551  TTTTTGAAGAAAAAGATTGCTGAATTGGAAATGCAAGTTTCTAAACCAAA

601  TCAAGCAAATCCTGATGATACACAACGCTCTGATCTTGC
                                          └──→ VECTOR
```

FIG. 19

LACTOCOCCUS PROMOTER AND SIGNAL SEQUENCES FOR EXPRESSION IN BACTERIA

BACKGROUND OF THE INVENTION

1. Field of the Invention

The present invention relates to the field of molecular biology, and, more particularly, to the fields of recombinant genetics and genetic engineering. The invention further relates to DNA sequences, derived from *Lactococcus lactis*, which are useful as promoters and promoter/secretion promoting signals for heterologous or homologous expression in bacteria. In another aspect, the invention relates to vectors, such as plasmics, comprising the sequences of the present invention, and to host cells transformed with such vectors. Yet additional aspects of the present invention are related to methods for producing desired heterologous or homologous peptides or proteins employing the sequences, vectors, or transformed hosts of the invention. By means of the invention, greatly improved heterologous and homologous expression and secretion may be achieved.

2. Description of Related Art

The lactic acid bacteria are of great commercial importance for, among other things, their ability to carry out fermentation, a process in which organic compounds serve as both electron donors and electron acceptors. Lactic fermentation reduces pyruvate to lactate in a single step reaction catalyzed by NAD-linked lactic dehydrogenase, without gas formation, and is the first stage in cheese manufacture. Thus, lactic fermentations are responsible for souring, or acidification, of milk and certain other foods, which allows for anaerobic preservation. Further, these processes are involved in the formation of interesting and desirable food and beverage flavors.

The lactic acid bacteria are thus of significant commercial importance. To-date, however, much of the work involving recombinant genetics has been carried out in other bacteria, such as *E. coli*. One result of this is that the genetics of the lactic acid bacteria are relatively less well understood or characterized. Inasmuch as there is a great deal of practical knowledge relating to the cultivation of lactic acid bacteria for commercial purposes, a continuing need exists for the application of recombinant genetic techniques to the understanding of these bacteria.

Information Disclosure Statement

In accordance with the requirements of 37 CFR §1.56, the following are concise explanations of documents known to Applicants or their attorney, submitted in accordance with 37 CFR §§1.97 and 1.98.

Applicants will submit hereafter on form PTO-1449 a listing of these documents in accordance with 37 CFR §1.98, together with copies of the listed documents.

Applicants do not waive any rights to appropriate action to establish patentability over any of the listed documents should they be applied as references against the claims of the present application.

This statement should not be construed as a representation that more material information does not exist or that an exhaustive search of the relevant art has been made.

Consideration of these documents, and making the same of record in the prosecution of the present application upon submission of the form PTO-1449 and copies of the documents listed therein, are respectfully requested.

de Vos, *Neth. Milk Dairy J.* 40:141–154 (1986), and *FEMS Microbiol. Rev.* 46:281–295 (1987), are review articles which disclose mesophilic lactic streptococcal host-vector systems used in cloning and expression of homologous and heterologous genes. Summaries of the properties of lactic streptococcal hosts and cloning vectors are set forth, as well as difficulties and issues related to successful transformation. Gene cloning strategies also are discussed, and sequences of several lactic streptococcal promoters, ribosome binding sites, and terminators are mentioned.

European patent application publication number 0 157 441 discloses certain shuttle vectors capable of expression in *B. subtilis*, *E. coli* and *Streptococcus lactis*, containing the replicon from the large ClaI fragment of the *S. cremoris* Wg2 plasmid pWV01. It is stated by the applicants that these vectors can give improved or new properties to lactic acid bacteria transformed therewith. Examples of the use of this system include the expression of genes for a protease and a chymosin precursor in *S. lactis*.

A number of other reports have appeared relating to the characterization of *S. cremoris* Wg2 protease activity. For example, Kok et al., *Applied Environmental Microbiol.* 50:94–101 (1985), disclose the cloning of a large (4.3 Md) HindIII fragment from the *S. cremoris* Wg2 plasmid pWV05, and its expression in *B. subtilis*. It is reported that this fragment contained two proteolytic proteins, and that it could be expressed in a proteinase-deficient *S. lactis* strain following protoplast transformation. van der Vossen et a., *Applied Environmental Microbiol.* 50:540–542 (1985), disclose several shuttle vectors derived from the largest ClaI fragment of the *S. cremoris* Wg2 plasmid pWV01, and the *B. subtilis* vector pPL608, carrying the *B. pumilus* chloramphenicol acetyltransferase (CAT) gene. The authors state that these vectors allow the isolation of promoter and transcription terminator signals in lactic streptococci. However, as pointed out subsequently by van der Vossen et al., *Applied Environmental Microbiol.* 53:2452–2457 (1987), fragments with promoter activity could be obtained only via precloning in *B. subtilis*, because of the low transformation efficiency of *S. lactis* protoplasts. The latter paper discloses the characterization of a number of *S. cremoris* promoters of various strengths, which were isolated partly via precloning in *B. subtilis* and partly by direct cloning in *S. lactis* with a pGKV210 plasmid. Several *S. cremoris* promoter nucleotide sequences are disclosed. Kok et al., *Applied Environmental Microbiol.* 54:239–244 (1988), disclose a deletion analysis of the *S. cremoris* Wg2 proteinase gene cloned in the heterologous host *S. lactis*. van de Guchte et al., *Applied Environmental Microbiol.* 55:224–228 (1989), disclose the construction of a pair of vectors for expression of heterologous genes in *Lactococcus lactis*, containing a multiple cloning site flanked by gene expression signals originating from *L. cremoris* Wg2. This system was used to express a fusion gene containing the eukaryotic hen egg white lysozyme (HEL) coding sequence in *L. lactis*. However, no lysozyme activity was detected from the expressed fusion protein, and the authors state that this was because the fusion protein was either inactive or was produced in too low a quantity to be detected.

Simons et al., *J. Dairy Sci.* 71 (Supp 1):Abstr. D64 (1988), discloses efficient expression vectors based upon the cryptic *S. lactis* plasmid pSH71 replicon and lactic streptococcal specific expression signals. It is stated that sequences resembling postulated *E. coli* and *B. subtilis* concensus sequences have been identified and function very efficiently in these hosts. It is further stated that these expression signals have been used for synthesis in lactic streptococci of β-galactosidase and chymosin.

Vos et al., *J. Dairy Sci.* 71 (Supp 1):Abstr. D65 (1988), discloses that *S. cremoris* SK11 contains a non-bitter cell wall-associated proteinase, of which the complete gene has been cloned and sequenced. It is stated that a DNA fragment containing this gene and another proteinase gene was cloned into a lactic streptococcal cloning vector (pNZ521) and expressed.

Kondo, *J. Dairy Sci.* 71 (Supp 1):Abstr. D125 (1988), discloses that development of gene transfer and host-vector systems in lactic streptococci have made it possible to study the genetics and plasmid biology of these industrially significant bacteria. It is stated that, basically, four methods of gene transfer exist: transduction, conjugation, protoplast fusion and transformation/-transfection. It also is stated that shuttle vector systems for cloning and analysis of lactic streptococcal genes in *Escherichia coli*, *Bacillus subtilis* and *Streptococcus sanguis* allow for detailed molecular analysis of genes and gene products.

de Vos, *J. Dairy Sci.* 71 (Supp 1):Abstr. D127 (1988), discloses that recently established host-vector systems have been used to study the organization and expression of plasmid located genes in mesophilic lactic streptococci *S. lactis* and *S. cremoris*. It is stated that most attention has been focussed on homologous genes important for use of these strains in industrial fermentation, and on heterologous genes which could be used to construct strains having novel properties. It also is stated that homologous genes encoding lactose and casein degradation events have been alayzed, as well as regulatory control of copy number of *S. lactis* plasmid pSH71, and that topogenic sequences which direct cellular location of expressed proteins have been identified.

Despite attempts by others, as illustrated by the preceeding discussion, there continues to exist a need for improved means and methods of homologous and especially heterologous expression in Gram-positive bacteria. Moreover, the present inventors are not aware of the existence of any significant studies involving the *Lactococcus lactis* subsp. lactis system.

SUMMARY OF THE INVENTION

Accordingly, the present inventors have discovered, isolated, cloned and sequenced novel promoters and promoter/secretion promoting signals from *Lactococcus lactis* subsp. lactis, which are useful in the production of heterologous and homologous proteins and peptides in *E. coli* and, especially, in Gram-positive bacteria.

In the course of elucidating the novel sequences of the present invention, it was necessary to design and construct certain vectors which would act as probes to identify *L. lactis* subsp. lactis promoters, and which were themselves novel. Accordingly, one embodiment of the present invention provides for a promoter probe-vector able to replicate in *E. coli*, *B. subtilis*, Lactococci and Lactobacillus, selected from the group consisting of the plasmids pKTH1734 and pKTH1736, the said plasmids constructed as shown in FIG. 5, or a functional derivative thereof. There is also provided the previously mentioned promoter probe-vector, further comprising mutliple cloning sites having nucleotide sequences as shown in FIG. 1, or a functional derivative thereof. Also provided is a promoter probe-vector able to replicate in *E. coli*, *B. subtilis*, Lactococci and Lactobacillus, comprising the plasmid pKTH1750, or a functional derivative thereof. *E. coli*, *B. subtilis*, Lactococci and Lactobacillus hosts transformed with any of these promoter probe-vectors comprise an additional embodiment of the invention.

Using the promoter probe-vectors of the invention, the present inventors were able to clone and sequence previously unknown and undescribed *L. lactis* subsp. lactis promoter and promoter/secretion signal promoting nucleotide sequences. Thus, in another embodiment, the present invention provides for a substantially pure nucleotide sequence as shown in FIGS. 9, 10, 11, 12, 13, 14, 15, 16, 17 or 19, or a functional or chemical derivative thereof. These sequences may be beneficially incorporated into plasmids, by means of which it has been possible to achieve enhanced heterologous protein expression in *E. coli* and, especially, in Gram-positive bacteria. Plasmids comprising these nucleotide sequences thus form another embodiment of the present invention.

Among the sequences and plasmids of the present invention are those which include *L. lactis* subsp. lactis-derived promoter sequences, exemplified by the sequences found in plasmids pKTH1798, pKTH1816, pKTH1817, pKTH1820, pKTH1821 and pKTH1874. Other sequences and plasmids of the invention include both the promoter and the secretion promoting signals, and are exemplified by the sequences found in plasmids pKTH1797, pKTH1798, pKTH1799, pKTH1801, pKTH1805, pKTH1806, pKTH1807 and pKTH1809. These plasmids and their respective nucleotide sequences form additional embodiments of the present invention.

In addition to the sequences and plasmids described above, however, an important teaching of the present invention is the discovery by the present inventors that the regulatory elements of those sequences and plasmids may be recombined to produce hybrid expression units which can function together to allow enhanced heterologous expression in *E. coli* and, especially, in Gram-positive bacteria. Thus, in another embodiment, there is provided according to the present invention a hybrid expression unit composed of a promoter sequence, exemplified by any of the sequences found in plasmids pKTH1789, pKTH1816, pKTH1817, pKTH1820, pKTH1821 and pKTH1874, together with a secretion promoting signal derived from sequences and plasmids of the invention including both the promoter and the secretion promoting signals, such as are exemplified by the sequences found in plasmids pKTH1797, pKTH1798, pKTH1799, pKTH1801, pKTH1805, pKTH1806, pKTH1807 and pKTH1809. In one illustrative non-limiting embodiment, there is provided a hybrid expression unit wherein the promoter sequence is derived from the plasmid pKTH1817, and wherein the secretion signal sequence is derived from the plasmid pKTH1807.

In another aspect, the present invention is directed to *E. coli* and, especially, to Gram-positive host cells transformed with any of the sequences or plasmids of the invention. In accordance with the invention, of course, the plasmids may additionally comprise a nucleotide sequence encoding one or more homologous or heterologous proteins or peptides which it is desired to express primarily in a Gram-positive host. Host cells according to the invention are selected from the group consisting of *E. coli* and the Gram-positive *B. subtilis,* Lactococci and Lactobacillus hosts.

An additional embodiment of the present invention provides for a method of heterologous or homologous protein or peptide expression, comprising transforming *E. coli* or a Gram-positive host cell with a plasmid according to the invention (which plasmid also comprises the nucleotide sequence encoding the desired protein or peptide); culturing the transformed host cell in a suitable medium under conditions allowing expression of said protein or peptide, and recovering the expressed protein or peptide from said host cell or said medium.

These embodiments, as well as additional embodiments of the present invention, will become more apparent and easily understood to those of skill by reference to the following detailed description of the invention.

BRIEF DESCRIPTION OF THE DRAWINGS

FIG. 1: Oligonucleotides using in cloning multiple cloning sites (MCS) in the vector pKTH1736.

FIG. 9: Sequence of pKTH1816. The black dot above the sequences indicates the start site of mRNA; if it is in parenthesis it indicates a possible secondary start site (this is true generally for all figures showing plasmid sequences where applicable).

FIG. 10: Sequence of pKTH1817.

FIG. 11: Sequence of pKTH1820.

FIG. 12: Sequence of pKTH1874. The total number of bases is 253. The DNA sequence composition is 92A; 39C; 49G; and 73T. (Sequence name NMMPRO1K.)

FIG. 13: Sequence of pKTH1789 (Strand L).

FIG. 14: Sequence of pKTH1797.

FIG. 15: Sequence of pKTH1798.

FIG. 16: Sequence of pKTH1799.

FIG. 17: Sequence of pKTH1801.

FIG. 18: Oligonucleotide primers used in the construction of the hybrid vector of FIG. 20.

FIG. 19: Sequence of pKTH1821.

DESCRIPTION OF THE PREFERRED EMBODIMENTS

Figure 2:
FIG. 2: The size of in vitro synthesized β-lactamase precursors. Lane 1, β-lactamase control; lane 2, pKTH1797; lane 3, pKTH1798; lane 4, pKTH1799; lane 5, pKTH1801; lane 6, $M_r$ standard. See text for technical details.

In the following description, reference will be made to various methodologies known to those of skill in the art of molecular genetics and biology. Publications and other materials setting forth such known methodologies to which reference is made are incorporated herein by reference in their entireties as though set forth in full.

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al, *Principles of Gene Manipulation: An Introduction to Genetic Engineering*, 2d edition, University of California Press, publisher, Berkeley, Calif. (1981); and Maniatis, T., et al., *Molecular Cloning: A Laboratory Manual*, Cold Spring Harbor Laboratory, publisher, Cold Spring Harbor, N.Y. (1982). General principles of microbiology are set forth, for example, in Davis, B. D., et al., *Microbiology*, 3d edition, Harper & Row, publishers, Philadelphia, Pa., (1980).

By "promoter" is meant generally a region on a DNA molecule to which an RNA polymerase binds and initiates transcription. The nucleotide sequence of the promoter determines both the nature of the enzyme that attaches to it and the rate of RNA synthesis. As used herein, "promoter" preferably refers to nucleotide sequences derived from *L. lactis* subsp. lactis. Similarly, by "promoter/signal promoting sequence" is meant generally a nucleotide sequence which comprises, in addition to a promoter sequence, a sequence encoding a 16–35 amino acid segment, usually containing hydrophobic amino acids that become embedded in the lipid bilayer membrane, which allows for the secretion of an accompanying protein or peptide sequence from the host cell, and which usually is cleaved from that protein or peptide. As used herein, "promoter/signal promoting sequence" preferably refers to nucleotide sequences derived from *L. lactis* subsp. lactis.

By "hybrid expression unit" is meant any combination of the promoter and promoter/signal promoting sequences of the invention to produce a different or distinct sequence which retains expression or expression and secretion functions. The manner and methods of combining the sequences of the invention to produce numerous such hybrid expression units are well known to those of skill, and are described and exemplified herein. Further, those skilled in the art who have fully appreciated the teachings of the present invention will recognize that it will be possible and even desirable to produce such hybrid expression units in order to optimize expression and secretion of given heterologous or homologous proteins or peptides, and that the same will be accomplished using well-known recombinant methods with the exercise of merely routine skill.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector.

By "cDNA library" is meant a collection of recombinant DNA molecules containing cDNA inserts which together comprise sequences expressed from the genome of an organism. Such a cDNA library may be prepared by methods known to those of skill, and described, for example, in Maniatis et al., *Molecular Cloning: A Laboratory Manual,* supra. Generally, RNA is first isolated from the cells of an organism from whose genome it is desired to clone a particular gene. Preferred for the purposes of the present invention are cell lines of bacteria.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages. Preferred for the purposes of the present invention, however, are plasmids comprising promoters and promoter-secretion promoting sequences derived from *L. lactis*.

By "substantially pure" is meant any protein of the present invention, or any gene encoding any such protein, which is essentially free of other proteins or genes, respectively, or of other contaminants with which it might normally be found in nature, and as such exists in a form not found in nature. This term also may be used with reference to the nucleotide sequences encoding the promoters and promoter-secretion promoting sequences of the invention derived from *L. lactis*. By "functional derivative" is meant the "fragments," "variants," "analogs," or "chemical derivatives" of a molecule. A "fragment" of a molecule, such as any of the DNA sequences of the present invention, is meant to refer to any nucleotide subset of the molecule. A "varient" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th ed., Mack Publishing Co., Easton, Pa. (1980).

Similarly, a "functional derivative" of the present invention is meant to include "fragments," "variants," or "analogues" of a gene, which may be "substantially similar" in nucleotide sequence, and which encode a molecule possessing similar activity.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, Shine-Dalgarno sequence, and the like.

If desired, the non-coding region 3' to the gene sequence coding for the protein may be obtained by the above-described methods. This region may be retained for its transcriptional termination regulatory sequences, such as termination. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a heterologous protein encoding sequence) are said to be operably linked if the nature of the linkage between the two DNA sequences does not (1) result in the introduction of a frame-shift mutation, (2) interfere with the ability of the promoter region sequence to direct the transcription of the heterologous protein gene sequence, or (3) interfere with the ability of the heterologous protein gene sequence to be transcribed by the promoter region sequence. Thus, a promoter region would be operably linked to a DNA sequence if the promoter were capable of effecting transcription of that DNA sequence.

Thus, to express the protein, transcriptional and translational signals recognized by an appropriate host are necessary.

In a preferred embodiment, the introduced sequence will be incorporated into a plasmid vector capable of autonomous replication in the recipient host. Any of a wide variety of vectors may be employed for this purpose. Factors of importance in selecting a particular plasmid vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184 πVX). Such plasmids are, for example, disclosed by Maniatis, T., et al. (In: *Molecular Cloning, A Laboratory Manual*, Cold Spring Harbor Press, Cold Spring Harbor, N.Y. (1982). Bacillus plasmids include pC194, pC221, pT127, etc. Such plasmids are disclosed by Gryczan, T. (In: *The Molecular Biology of the Bacilli*, Academic Press, NY (1982), pp. 307-329). Particularly preferred vectors according to the invention are those which are able to replicate in *E. coli, B. subtilis*, Lactococci and Lactobacillus.

Once the vector or DNA sequence containing the construct(s) has been prepared for expression, the vector or DNA construct(s) may be introduced into an appropriate host cell by any of a variety of suitable means, including such biochemical means as transformation, transfection, conjugation, protoplast fusion, calcium phosphate-precipitation, and application with polycations such as diethyl-aminoethyl (DEAE) dextran, and such mechanical means as electroporation, direct microinjection, and microprojectile (biolistic) bombardment (Johnston et al., *Science* 240(4858): 1538 (1988)), etc.

After the introduction of the vector, recipient cells are grown in a selective medium, which selects for the growth of vector-containing cells. Expression of the cloned gene sequence(s) results in the production of the desired heterologous or homologous protein, or in the production of a fragment of this protein.

The expressed protein may be isolated and purified in accordance with conventional conditions, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. In a preferred embodiment, the expressed protein will also be secreted from the host cell when any of the promoter/secretion promoting signals of the invention are employed, with the advantage that isolation and purification procedures will be simplified.

Alternatively, the expressed heterologous protein or functional derivative thereof, may be isolated by the use of antibodies directed against the desired protein or functional derivative. Such antibodies may be obtained by well-known methods.

The manner and method of carrying out the present invention may be more fully understood by those of skill by reference to the following examples, which examples are not intended in any manner to limit the scope of the present invention or of the claims directed thereto.

EXAMPLE I

Bacterial Strains and Growth Media

The bacterial strains used are listed in Table 1.

TABLE 1

Bacterial Strains, Genotypes and Sources

| Strain | Our Code | Genotype | Reference or Source |
|---|---|---|---|
| *Escherichia coli* TG1 | ERF173 | K12Δ(lac pro) supE thi hsdD5 F'tra35 proA+, B+ laqI$^q$ lacZ M15 | EMBL (European Molecular Biology Laboratory) |
| *Bacillus subtilis* | BRB1 | metB5 sacA321 | Palva I, Gene 19:81-87 (1982) |
| *Lactococcus lactis*[1] subsp *lactis* MG1614 | GRS5 | transformable | Valio[2] Gasson M. |
| *Lactobacillus plantarum* NRLB192 | | | Valio |

[1]Formerly called *Streptococcus lactis*.
[2]Valio Finnish Co-operative Dairies' Association.

For propagating *E. coli* and *B. subtilis* strains, Luria broth (Lennox, *Virology* 1:190-206 (1955)) was used; for *L. lactis* M17G or M17GS broth (Terzaghi et al., *Appl. Microbiol.* 29:807-813 (1975)) and for *L. plantarum*, MRS broth (De Man et al., *J. Appl. Bacteriol.* 23:130-135 (1960)) was used.

TABLE 2

Media and Markers Used for Various Hosts

| Host | Growth | Antibiotic |
|---|---|---|
| *E. coli* ERF173 | Luria | ap 50 μg/ml or cm 11 μg/ml tc 12,5 μg/ml |
| *B. subtilis* BRB1 | Luria | cm 5 μg/ml, km 10 μg/ml |
| *L. lactis* GRS5 | M17G, M17GS | cm 4-5 μg/ml |
| *L. plantarum* | MRS | cm 4-5 μg/ml |

| ORIGINATING PLASMIDS | |
|---|---|
| pVS2 | shuttle vector between *E. coli, B. subtilis, L. lactis, L. plantarum* 5 kb, em$^r$, cm$^r$ Described by von Wright et al., Appl. Environm. Microbiol. 53:1584-1588 (1987). |
| pAMB11 | Bacillus vector, 5.3 kb, km$^r$, cm$^r$ Described by Zukowski et al., (Gene 46:247-255 (1986)). |
| pKTH33 | A deletion derivative of pHV33, a chimera between pBR322 and pC194. Described by Palva, Ph.D. thesis, University of Helsinki (1983). 4.6 kb, ap$^r$, cm$^r$ in *E. coli*, cm$^r$ in *B. subtilis* (Michel et al., Gene 12:147-154 (1980)). |
| pSH71 | Cryptic *L. lactis* plasmid, 2 kb Described by Gasson, J. Bacteriol. 154:1-9 (1983). |
| pBR322 | 4.4 kb, ap$^r$, tc$^r$ Described by Sutcliffe, J. G., Cold Spring Harbor Symp. Quant. Biol. 43:77 (1979); and Peden, K.W.C., Gene 22:277 (1983). |

TABLE 2-continued

Media and Markers Used for Various Hosts

| | |
|---|---|
| pPL603 | Promotor cloning vector for *B. subtilis* 4.8 kb, km$^r$ |
| | Described by Duval et al., J. Bacteriol. 158:784-790 (1984). |
| pKTH78 | Bacillus vector 5.5 kb, km$^r$ |
| | Contains TEM-β-lactamase gene. |
| | Described by Palva et al., Proc. Natl. Acad. Sci. USA 79:5582-5586 (1982). |

METHODOLOGY USED

DNA Isolations and Modifications

Rapid isolation of plasmid DNA from *E. coli* for screening of the clones was done according to Holmes et al. (Anal. Biochem. 134:193-197 (1980)). DNA for restriction enzyme digests was prepared by the method of Birnboim et al. (*Nucl. Acids Res.* 7:1513-1523 (1979)) either from 1 ml or 10 ml of liquid culture. RNAse (Boehringer) was added prior to restriction enzyme treatments.

Isolation of plasmid DNA from *B. subtilis* was carried out according to Gryczan et al. (*J. Bacteriol.* 134:318-329 (1978)). Isolation of plasmid DNA from *L. lactis* subsp. lactis was carried out according to Andersson et al., (*Appl. Environm. Microbiol.* 46:549-552 (1983)), both for small-scale and large-scale isolations.

Chromosomal DNA from *L. lactis* subsp. lactis was isolated by the above-described method; only the chromosomal band was collected from CsCl-runs.

Further purification of DNA, if needed, was done by CsCl-EtBr density gradient centrifugation, regardless of the source of the DNA preparation.

Restriction enzyme digestions were performed according to the manufacturer's recommendations (Boehringer, BRL, Promega). Selected restriction fragments were obtained by separation of the digested DNA on 0.8% agarose gel electrophoresis (Sharp et al., *Biochemistry* 12:3055-3063 (1973)) after which DNA extraction and purification was performed by a phenol-liquid nitrogen freezing method as follows: a slice of agarose containing the desired fragment was transferred to a siliconized Eppendorf tube and mashed with a glass rod. About 250 μl TE-buffer was added together with an equal volume of phenol. After thorough mixing in a Vortex shaker, the tube was immersed in liquid nitrogen until frozen. The phases were separated by centrifugation at 1200 rpm for 15 minutes, after which phenol extraction was repeated and the resulting aqueous layer treated with ether and ethanol-precipitated.

As an alternative method for DNA fragment isolation, the procedure described by Hawkins et al. (*Curr. Genet.* 9:305-311 (1985)) was used, or the isolation was done by electroelution with a "Model UEA Undirectional Electroelutor Analytical" apparatus (International Biotechnologies, Inc.) according to the manufacturer's instructions.

Modification of the Ends of DNA Fragments

For the generation of blunt-end fragments, the Klenow fragment of DNA polymerase I (Promega) was used. As alternative methods, T4 DNA polymerase (Promega) or mung bean nuclease (Promega) also were used. For dephosphorylation of 5'-phosphorylated ends, calf intestinal phosphatase (CIP, Boehringer) was used. T4 polynucleotide kinase (Promega) was used for phosphorylation of the 5'-hydroxyl ends.

The ends of the DNA fragments were joined by T4 DNA ligase (Promega). All modifying enzymes were used according to manufacturer's recommendations.

DNA Transformations

Transformation of *E. coli* cells was accomplished by the method of Hanahan (*J. Mol. Biol.* 166:557-580 (1983)). *B. subtilis* cells were transformed by the method of Gryczan et al. (*J. Bacteriol.* 134:318-329 (1978)). *L. Lactis* protoplast transformation was carried out according to von Wright et al. (*Appl. Environm. Microbiol.* 50:1100-1102 (1985)). *L. plantarum* transformation by electroporation was performed by the method of Aukrust et al. (submitted for publication). The method is described below.

*Lactobacillus plantarum* transformation by Electroporation

Electroporation. For electroporation experiments, cells were grown to an optical density of 0.5-1.0 ($A_{600}$), chilled on ice, harvested by centrifugation, washed, and resuspended in electroporation buffer (EB) to a cell density of about $10^9$ cells/ml. An aliquot of 0.8 ml ice-cold cell suspension was mixed with 0.5-1.0 μg of plasmid DNA. Cells were kept on ice before and after electroporation in buffer (PEB). Electroporation was performed using a GenePulser TM apparatus (BioRad Laboratories, Richmond, USA) at a constant capacitance of 25 μFD, with a field strength between 1250 and 6250 V/cm for whole cells and between 1250 and 5000 V/cm for osmosensitive cells. Electroporation of intact cells was carried out in EB as described in the GenePulser TM operating instructions (BioRad Laboratories, Richmond, USA). Osmosensitive cells were electroporated in protoplast electroporation buffer (PEB): 0.5M raffinose, 7 mM sodium phosphate pH 7.4, $MgCl_2$ up to 50 mM.

Enzymatic Assays

β-lactamase was assayed according to O'Callaghan et al. (*Antimicrob. Ag. Chemother.* 1:238-288 (1972)). Cell and supernatant fractions were separated by centrifugation after growth in appropriate liquid medium.

Chloramphenicol acetyltransferase (CAT) assay. Cells were grown to log phase, and 1 ml cultures were collected for enzyme activity analysis. Cells were harvested by centrifugation, washed with 50 mM sodium phosphate buffer pH 7, and suspended in 0.2 ml of the same buffer containing 4 ml/ml lysozyme. Cells were incubated for 30 minutes at 37° C., after which they were disrupted by sonication (4×15 seconds, using a Bransonic sonicator; after each 15 seconds of sonication, the medium was cooled for 30 seconds in an ice bath). After sonication, the cell debris was pelleted by centrifugation. 50 μl of the supernatant was used for enzyme assay. CAT-activity was measured according to the method of Shaw, W. V., *Meth. Enzymol.* 43:737-755 (1975)).

Catechol 2,3-dioxygenase was assayed according to Zukowski et al. (*Proc. Natl. Acad. Sci. USA* 80:1101-1105 (1983)).

RNA Methods

Isolation of RNA

RNA was isolated according to the method of van der Vossen et al. (*Appl. Environm. Microbiol.* 53:2452-2457 (1987)), except that cells were cultured in 10 ml of M17G-medium containing 5 μg/ml chloramphenicol until Klett 80 was reached, and that the RNA (and DNA) was precipitated with ethanol (the medium was made to 0.5M with 3M NaAc, and 3 volumes of ethanol were added). The pellet was dissolved in distilled water. The DNA was digested with RNAse-free DNAase I (Promega) in 40 mM Tris-HCl (pH 7.9), 10 mM NaCl, 6 1 mM MgCl₂ buffer containing 10 mM dithiothreitol and 40 U/ml ribonuclease inhibitor RNAsin ® (Promega). After incubation for 10 minutes at 37° C., the reaction mixture was extracted once with phenol, phenol-chloroformisoamyl-alcohol (25:24:1, vol/vol) and chloroform-isoamylalcohol (24:1 vol/vol). The RNA was precipitated with ethanol and the pellet was dissolved in 75 μl of water.

Northern Transfer and Hybridization

To estimate the length of the RNAs transcribed by the cloned promoter or promoter/signal sequence fragments and to study the strength of the promoters, Northern analysis was made. The RNA gel was run and Northern transfer to nictrocellulose membrane (Schleicher and Schuell) was done according to Williams et al. (in, "Nucleic Acid Hybridization—A Practical Approach," Hames et al. (eds.), IRL Press, pp. 139-160 (1985)).

To detect the RNA species, the nitrocellulose filter was prehybridized in 0.06M sodium citrate (4×SSC), 50 mM sodium phosphate buffer (pH 6.5), 5×Denhardt (Biochem. Biophy. Res. *Commun.* 23:641-646 (1966)), 0.2% sodium dodecyl sulphate (SDS), and 200 μg/ml denatured herring sperm DNA (Sigma). Incubation was done for one to two hours at 65° C. Hybridization was done in the same medium containing nick-translated probe ($10^6$ cpm/ml). After hybridization, the filter was washed (1-2×) with 0.03M sodium citrate (2×SSC), 0.2% SDS, and incubated at 37° C. for 30 minutes and for 30 minutes at 55° C.

Primer Extension

The transcriptional start sites were determined by primer extension. To 15 μl RNA (5 to 10 μg) primer (0.2 pmol of 20 base oligonucleotide) mixture, 15 μl 2×hybridization buffer (100 mM Tris-HCl, pH 8.3, 2 mM EDTA, 0.8M NaCl) was added. The mixture was heated to 95° C. for 2 minutes and allowed to cool to room temperature over a two-hour period by gradually lowering the thermostat of the water bath.

The RNA-primer hybrid was precipitated with ethanol, and the pellet was dissolved in 5 μl of 2×reaction buffer (100 mM Tris-HCl, pH 8.3 at 42° C., 20 mM DTT, 12 mM MgCl₂, 100 mM KCl, 0.5 mM dATP, dTTP and dGTP and 50 μg/ml antinomycin C₁ (Boehringer)). To this mixture, 1.5 μl of deoxycytidial ($\alpha$-$^{32}$p) triphosphate (3000 Ci/mmol, 10 mCi/ml, Amersham), and 40 U of RNAsin ® 7 U AMV Reverse transcriptase (Promega) were added, and the total reaction volume was made to 10 μl with water. The reaction mixture was incubated for 15 minutes at 42° C., after which 0.5 μl of 10 mM dCTP (chase) was added, and incubation was continued at 42° C. for 1 hour and 45 minutes.

Subsequently, the reaction mixture was extracted with phenol and phenol-chloroform-isoamylalcohol (25:24:1), and precipitated with ethanol. The reverse transcriptase reactions were analyzed by electrophoresis on a standard sequencing gel. Sequencing reactions of one of the promoter constructions were used as a size marker and were run in parallel with the reverse transcriptase (RT) reactions.

Other Methods

In vitro translation of pre-β-lactamase was performed with a DNA expression system (in vitro DNA Directed, Prokaryotic by NEN Products, DuPont), after which the products were separated by SDS-PAGE according to Laemmli (*Nature* (London) 227:680–685 (1970)) and subjected to fluorography.

DNA Sequencing

All DNA sequencing was based on the Sanger method (*Proc. Natl. Acad. Sci. USA* 80:3963-3965 (1977)). For plasmid sequencing, a Sequenase ™ (United States Biochemical Corporation, USB) system was used, as described by Hattori et al. (*Anal. Biochem.* 152:232-238 (1986)).

Oligonucleotide Synthesis

Oligonucleotide synthesis of primers for sequencing and polymerase chain reactions were performed by phosphoramidite chemistry (Beaucage et al., *Tetrahedron Letters* 22:1859-1862 (1981)) using Applied Biosystems DNA synthesizer model 381A.

PCR-polymerase chain reaction: Amplification of specific DNA fragments was accomplished by GeneAmp ™ DNA Amplification kit as described by Saiki et al. (*Science* 239:487-491 (1988)) and the DNA Thermal Cycler (both from Perkin Elmer-Cetus). Taq polymerase was purchased from Perkin Elmer-Cetus.

EXAMPLE II

Construction of a Promoter Probe Vector

For the screening of chromosomal DNA fragments containing promoter-like activity, a promoter probe-vector able to replicate in *E. coli, B. subtilis,* Lactococci and Lactobacillus was constructed.

The replication origin for the shuttle vector was isolated from the plasmid pSH71. The plasmid pSH71 was digested with restriction enzyme ClaI to create two fragments of about 1.7 kb and 0.3 kb, the larger one of which contained the replication origin. The sticky ends were filled in with the Klenow fragment. The mixture was run in an agarose gel to isolate the large DNA fragment, and the DNA was eluted from the gel by electroelution.

To the replication fragment, two antibiotic selection markers were added: the gene coding for tetracycline was isolated from the plasmid pBR322, and the gene coding for erythromycin resistance was isolated from the plasmid pVS2. In order to get the gene fragment coding for tetracycline resistance, pBR322 was digested with EcoRI and PvuII. The sticky ends created by EcoRI were filled in with the Klenow fragment, the mixture was run in an agarose gel, the tetracycline gene-containing fragment was isolated, and the DNA fragment (about 2 kb) was eluted from the gel by electroelution.

Figure 4:
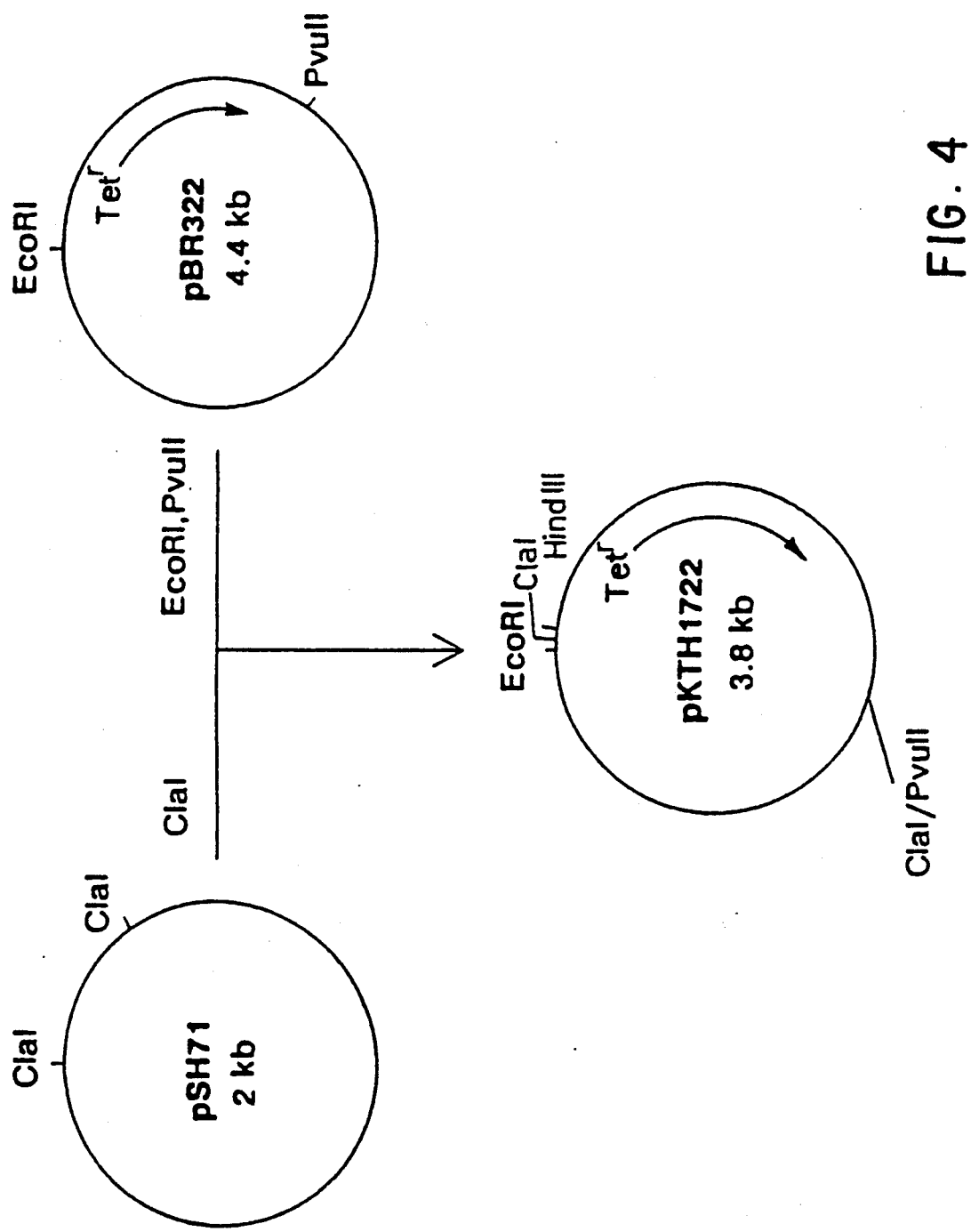
FIG. 4: Construction of vector pKTH1722.

The ClaI fragment containing the pSH71 replication origin and the DNA fragment containing the tetracycline gene were ligated and transformed into competent *E. coli* ERF173 cells. Transformants were selected by plating the transformation mixture on Luria-agar plates containing 12.5 μg/ml tetracycline. The structure of the plasmid was verified by restriction enzyme digestions. To this new plasmid, designated pKTH1722 (FIG. 4), the second resistance marker was added. pKTH1722 was linearized by XmnI digestion. The erythromycin gene was isolated from the plasmid pVS2 by HindIII-ClaI digestion, and the sticky ends were filled in with the Klenow fragment. The mixture was run in an agarose gel, the gel fragment containing the erythromycin gene was isolated, and the DNA fragment eluted from the gel by electroelution.

Figure 5:
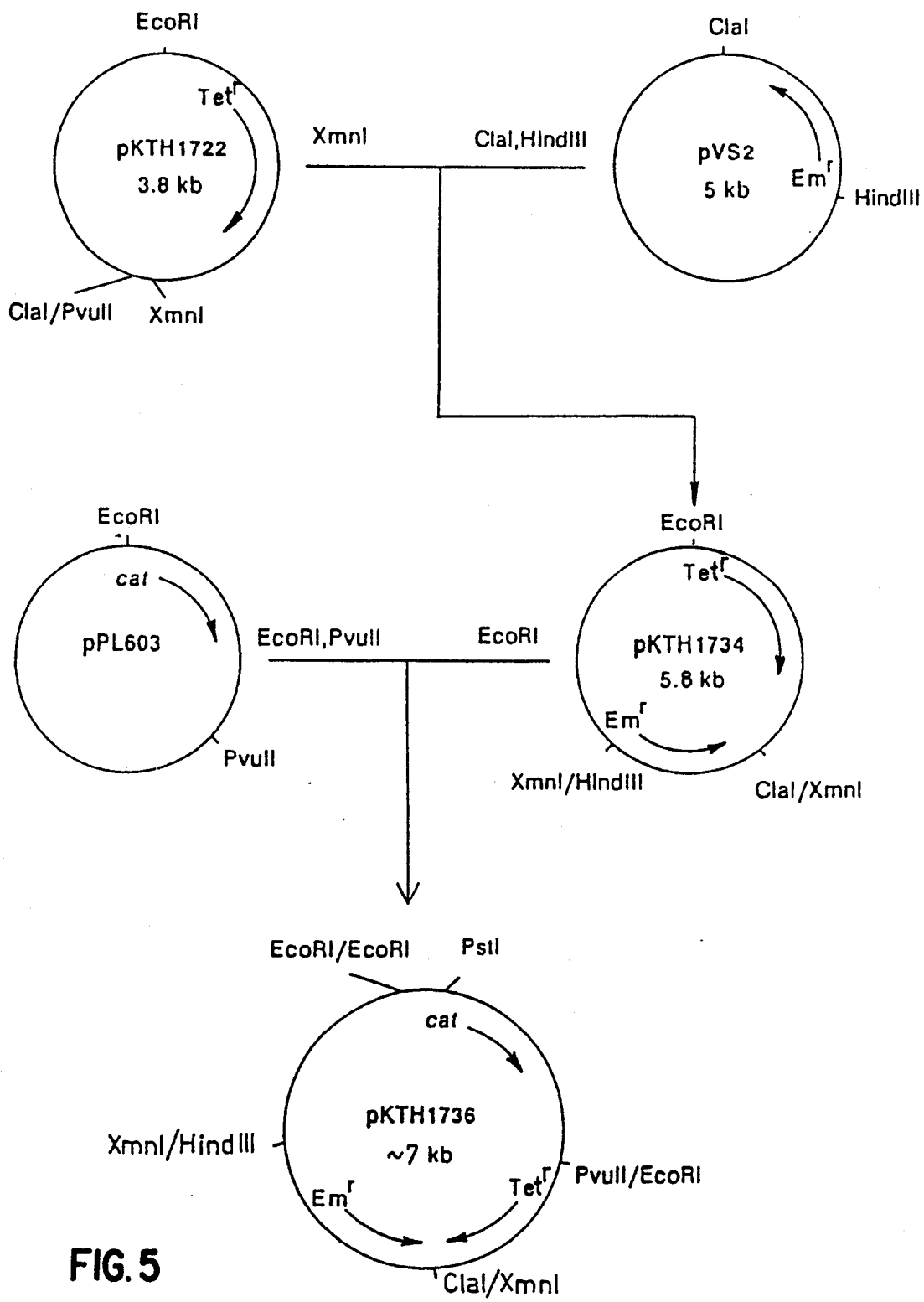
FIG. 5: Construction of vectors pKTH1734 and pKTH1736.

The linearized plasmid pKTH1722 and the erythromycin gene-containing DNA fragment were ligated, the ligated mixture was transformed into competent *E. coli* ERF173 cells, and the mixture was plated on Luria agar plates containing 12.5 µg/ml tetracycline. Transformants were screened by their ability to grow on Luria-agar plates containing 100 µg/ml erythromycin. Plasmid isolation was done from erythromycin resistant colonies and the presence of the gene was verified by restriction enzyme digestions. One correct plasmid construction was named pKTH1734 (FIG. 5).

For the construction of the promoter probe plasmid, a promoterless gene coding for chloramphenicol acetyltransferase from the plasmid pPL603 was ligated to the plasmid pKTH1734. pKTH1734 was linearized by EcoRI digestion, and the sticky ends were made blunt by the Klenow fragment. The promoterless CAT gene was isolated from the plasmid pPL603 by EcoRI-PvuII digestion, the sticky ends were filled in with Klenow-fragment, and the mixture was run on an agarose gel. The CAT gene-containing DNA fragment (about 1.7 kb) was isolated by the phenol-liquid nitrogen freezing method as described above.

The linearized plasmid pKTH1734 and the CAT gene-containing DNA-fragment were ligated and transformed to *E. coli* ERF173 cells. The inserts were screened by isolating plasmids and checking the restriction enzyme recognition patterns by digestions. The plasmid pKTH1736 was obtained (FIG. 5).

To further improve the vector, a DNA fragment containing multiple cloning sites (MCS) was added in front of the cat gene. pKTH1736 was linearized by PstI digestion. The MCS-sequence was constructed from two synthetic 21 base single-stranded oligonucleotides (FIG. 1), which were annealed in vitro. The ends of the MCS fragment were constructed so that, when ligated to PstI site, only one functional PstI site was formed. After ligation of the MCS segment to linearized pKTH1736, the mixture was transformed into competent *E. coli* ERF173 cells, and the MCS sequence-containing transformants were screened by isolating plasmids and doing restriction enzyme digestions.

Figure 6:
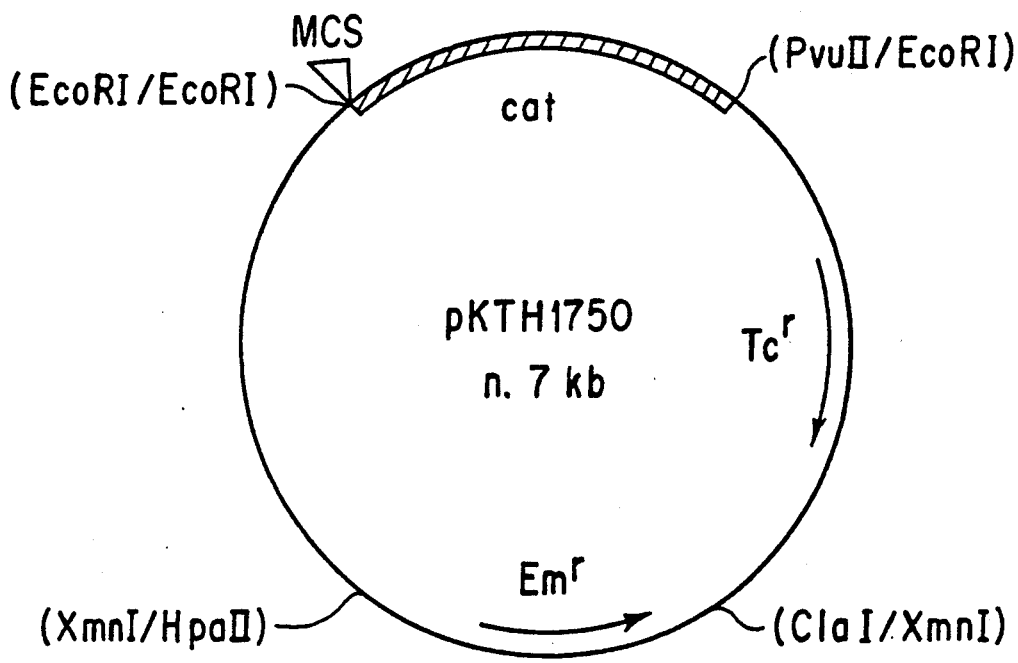
FIG. 6: Promoter probe vector pKTH1750.

To check that the MCS sequence was present in the vector only once, the plasmid obtained by the above procedure was digested with EcoRI and ligated to itself in a dilute medium and transformed to *E. coli* ERF173. The promoter probe vector pKTH1750 was obtained from this transformation (FIG. 6).

EXAMPLE III

Screening for Lactococcus Promoter Fragments by a Promoter Probe Vector pKTH1750

The promoter probe plasmid pKTH1750 can replicate in *E. coli*, *B. subtilis*, and *L. lactis*. The promoters were screened both in *B. subtilis* and in *L. lactis*. Lactococcus chromosomal DNA, digested with Sau3A, was ligated with BglII-digested pKTH1750 in a molar ratio of 2:1 (insert:vector DNA). The mixture was transformed to *L. lactis* GRS5 cells and plated on M17GS-cm (4µg/ml) plates, and also to *B. subtilis* BRB1 cells and plated on Luria-cm (5 µg/ml) plates. Only those transformants which contained promoter-like sequences in front of the CAT gene could grow on cm plates. The transformants obtained from *B. subtilis* transformation were further screened by Minimal Inhibitory Concentration assay (MIC). An overnight colony was suspended in a 1 ml 50 mM phosphate buffer pH 7.0. From the suspension, a streak was drawn with a glass rod for a set of Luria-cm plates containing different concentrations of cm (5, 15, 45, 100 µg/ml). Only transformants which could grow at a cm concentration of 45 to 100 µg/ml were transformed to *L. lactis* subsp. lactis GRS5.

Clones which were screened directly from *L. lactis* subsp. lactis, and clones which were first screened in *B. subtilis* and then transformed to GRS5, were characterized by CAT assay in both BRB1 and GRS5 hosts. Results for the clones pKTH1816 (FIG. 9), pKTH1817 (FIG. 10), pKTH1820 (FIG. 11), pKTH1821 (FIG. 19) are shown in Table 3.

Inserts were sequenced according to Sanger's dideoxy method, and were further characterized by Northern hybridization and primer extension.

TABLE 3

Expression of Chloramphenicol Acetyltransferase in *L. lactis* subsp. *lactis* and in *B. subtilis*

| Construction | Initial Cloning Host | CAT Activity in *L. lactis* GRS5 U/ml* | CAT Activity in *B. subtilis* BRB1 U/ml |
|---|---|---|---|
| pKTH1816 | GRS5 | 0.015 | 9.3 |
| pKTH1817 | GRS5 | 0.2 | 45.3 |
| pKTH1820 | BRB1 | 0.029 | 12.5 |
| pKTH1821 | BRB1 | 0.012 | 8.1 |
| GRS5 (control) or BRB1 | | 0.004 | 0.09 |

*Activity was measured as U/ml of culture medium as described herein.

EXAMPLE IV

Screening for Lactococcus Promoter Fragments by a Promoter Probe Vector pAMB11, Capable of Replication in *B. subtilis*

A promoter probe vector pAMB11 replicating in *B. subtilis* has been previously described (Zukowski et al., Gene 46:247-255 (1986)). This plasmid was opened with the restriction enzyme SmaI for a blunt-end cloning site or with BamHI to generate sticky ends.

Lactococcus chromosomal DNA was digested with Sau3A, which yielded fairly large (over 1000 pb) fragments, compatible for ligation with the BamHI-treated vector. For blunt-ended fragments, the chromosomal DNA was sonicated (Branson Sonifier, Branson Sonic Power Co.) to get 500–600 bp fragments. The extent of sonication was checked by running a small aliquot of treated sample in a 0.8% agarose gel with appropriate controls. The total sonicated DNA was then applied to a 0.8% agarose gel and electrophoresed. Fractions of about 600 bp were extracted and purified by phenol-liquid nitrogen treatment. The ends of the DNA fragments were treated with the Klenow fragment as described above.

The ligations, in both cases, were performed in a molar ratio of 2:1 (insert:vector DNA) under standard conditions, and the mixtures were transformed into *B. subtilis* BRB1.

Selection for promoter-containing plasmids was done by spraying the bacterial colonies with 0.5M catechol.

Transformants bearing a promoter sequence turned yellow due to the expression of catechol 2,3-dioxygenase, which converts catechol to 2-hydroxymuconic semialdehyde. The intensity of the yellow color is know to correlate with promoter strength. Plasmids pKTH1874 (FIG. 12) and pKTH1789 (FIG. 13) were obtained from the above transformations.

To study the production of catechol 2,3-dioxygenase in liquid culture (Table 4), the two strains were grown in Luria broth containing 10 μg/ml kanamycin. After 10 hours growth, 1 ml of cells was collected by centrifugation, treated, and the enzymatic activity determined according to the method described by Zukowski et al. (*Proc. Natl. Acad. Sci. USA* 80:1101–1105 (1983)).

TABLE 4

Lactococcus Chromosomal DNA Fragments Promoting the Expression of Catechol 2,3-dioxygenase in B. subtilis

| Construction | Size of Insert bp | Color[1] Intensity | Formation of 2-hydroxy-Muconic Semialdehyde (Catechol 2,3-dioxygenase Activity |
|---|---|---|---|
| pKTH1874 | 550 | + | 25.2 mmol/min |
| pKTH1789 | 500 | ++ | 207 mmol/min |
| control | No insert | − | <[2] |

[1]See text for details.
[2]Below detection limit.

DNA was extracted from the positive clones and subjected to plasmid sequencing.

EXAMPLE V

Screening for the Promoter/Signal Sequence Fragments Using Plasmid pKTH33

Plasmid pKTH33 contains the structural part of TEM-β-lactamase gene preceded by an EcoRI linker. Part of the plasmid originates from pBR322, allowing its replication in *E. coli*. If a sequence bearing an expression/secretion signal is inserted, in frame, with the marker gene β-lactamase, active enzyme is produced, which renders the transformants resistant to ampicillin. By plating the transformants directly on ampicillin plates, a positive selection for signal sequence fragments is obtained.

Plasmid pKTH33 was opened with EcoRI, treated with Klenow fragment to obtain blunt-end molecules, and purified by phenol extraction and ethanol precipitation.

The ligation mixture was transformed into *E. coli* ERF173 cells, and plated on Luria-ampicillin (50 μg/ml) plates. Several transformants were screened for β-lactamase activity by Nitrocefin assay on microtiter wells: 200 μl of Nitrocefin (Glaxo) in 50 mM K-phosphate buffer (pH 7.0) were pipetted into microtiter plate wells. Bacterial colonies were transferred from plates with a toothpick and suspended in Nitrocefin. Positive clones turned red after 1–30 minutes incubation at room temperature, whereas negative clones stayed yellow.

The minimal inhibitory concentration (MIC) of ampicillin for the positive clones was determined as described, except that cells were plated on Luria-ap plates containing ampicillin from 50–450 μg/ml. MIC was the highest concentration still supporting growth.

Clones which grew on ampicillin (400 μg/ml or greater) were chosen for further characterization.

Rapid isolation of plasmid DNA was performed on positive clones showing highest ampicillin resistance. The size of the chromosomal DNA insert was verified by restriction enzyme digests. Clones pKTH1797 (FIG. 14), pKTH1798 (FIG. 15), pKTH1799 (FIG. 16) and pKTH1801 (FIG. 17) are shown in Table 5.

TABLE 5

Plasmids Showing High Resistance to Ampicillin

| Construction | Size of Insert bp | MIC of ap μg/ml |
|---|---|---|
| pKTH1797 | 2,000 | 400 |
| pKTH1798 | 350 | >450 |
| pKTH1799 | 500 | 400 |
| pKTH1801 | 500 | >450 |

Inserts of pKTH1797, pKTH1798, pKTH1799 and pKTH1801 were sequenced according to the dideoxy method of Sanger, and analyzed for the presence of expression/secretion signals. By matching the three reading frames with the known reading frame of β-lactamase, the correct reading frame was determined. The length of the precursor proteins was compared with the data obtained from an in vitro transcription-translation assay (FIG. 2), in order to confirm the validity of the sequences.

β-lactamase activity of the four constructions was also determined by growing the appropriate strains in liquid medium (Table 6).

TABLE 6

Expression of β-lactamase in *E. coli*

| | Periplasm U/ml | Cells U/ml |
|---|---|---|
| pKTH1797 | 336 | 292 |
| pKTH1798 | 841 | 155 |
| pKTH1799 | 74 | 47 |
| pKTH1801 | nd[1] | nd[1] |
| pBR322[2] | 4,103 | 42 |
| ERF173 | <[3] | <[3] |

[1]Not determined.
[2]The source of the intact β-lactamase gene. The inserts were carried on *E. coli* vector pKTH33. To study periplasmic β-lactamase, cells were sonicated (4 × 15 seconds, Bransonic sonifier), cell debris was separated by centrifugation, and the supernatant taken as the periplasmic fraction.
[3]Below detection level.

EXAMPLE VI

Subcloning of Promoter/Secretion Signal Fragments into a Shuttle Replicon

Although the use of pKTH33 allowed direct selection of the desired fragments, the clones could not, as such, be propagated in Gram-positive bacteria. It was therefore necessary to change the replicon by subcloning the promoter/signal sequence fragments into the plasmid pVS2.

The insert plus the entire β-lactamase gene was cleaved off from pKTH1797, pKTH1798, pKTH1799, and pKTH1801 by ClaI-PvuII double digestion, and the desired fragments were extracted from a 0.8% agarose gel as previously described and treated with the Klenow fragment to generate blunt ends. The vector pVS2 was opened with HindIII, and treated with the Klenow fragment as above.

Ligation was performed in a molar ratio of 2:1 (insert:plasmid) under standard conditions, and the mixture was transformed into *E. coli* ERF173 cells and plated on Luria-cm (11 μg/ml) plates. The production of β-lactamase was checked by the Nitrocefin microtiterwell assay, as described. Rapid isolation of plasmid DNA was done for positive clones, and the size of the insert was verified by restriction enzyme digests.

Figure 7:
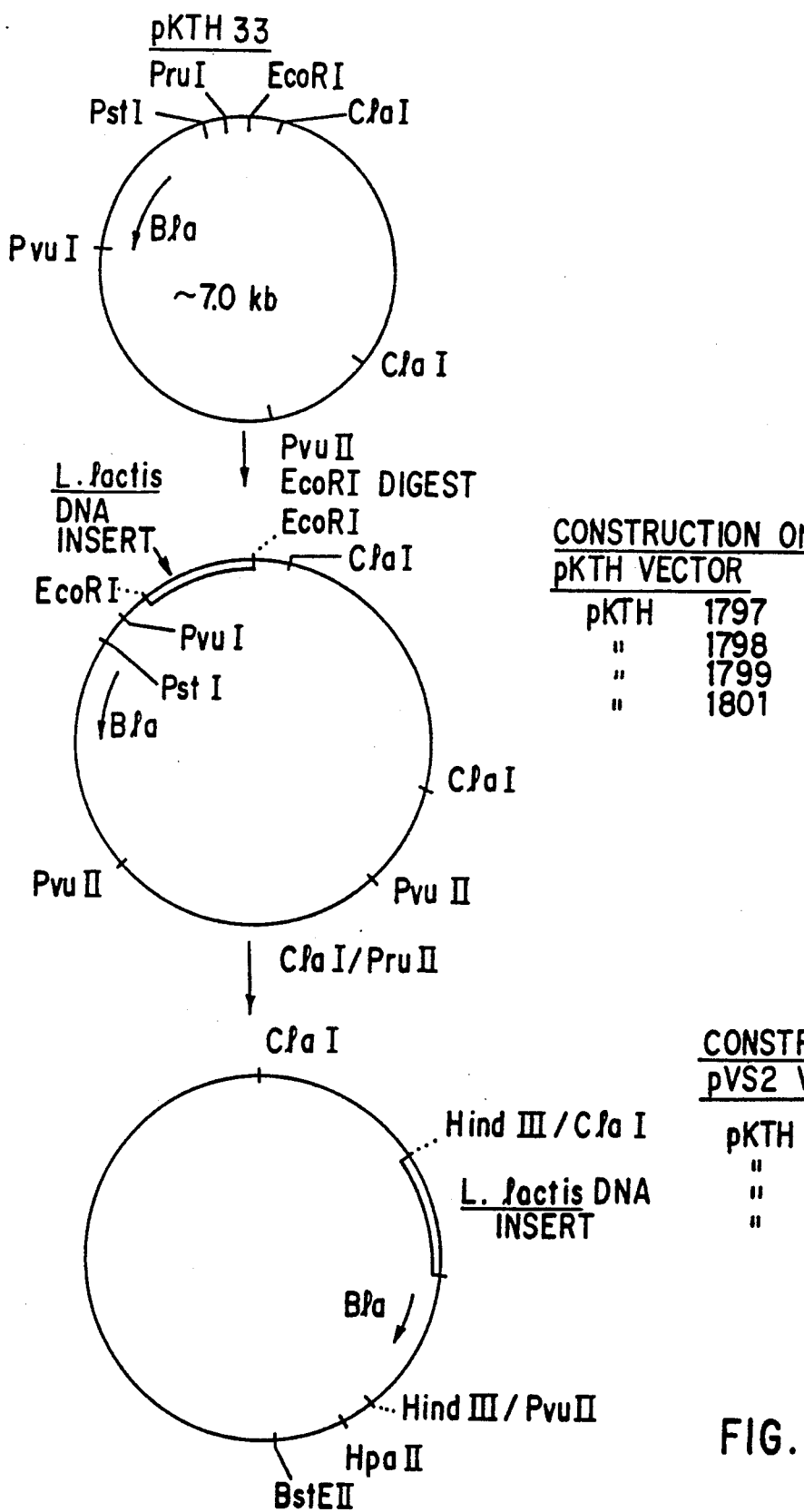
FIG. 7: Construction of vectors pKTH1797, pKTH1798, pKTH1799 and pKTH1801 based upon pKTH33, and of vectors pKTH1805, pKTH1806, pKTH1807 and pKTH1809 based upon pVS2.
Figure 8A:
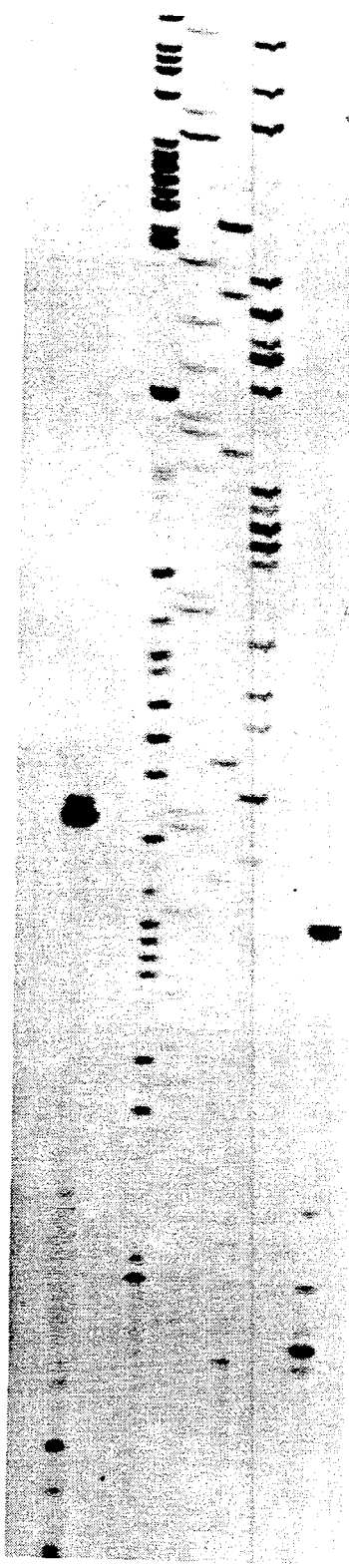
FIG. 8: Identification of the 5' end of mRNAs of *L. lactis* subsp. lactis promoter constructions by primer extension. Promoters were from constructions pKTH1817 (panel A, lane 1), pKTH1820 (panel A, lane 2), pKTH1821 (panel B, lane 3), and pKTH1816 (panel B, lane 4). The standard sequence in panel A was from promoter in construction pKTH1817 and in panel B from promoter in construction pKTH1816.
Figure 8B:
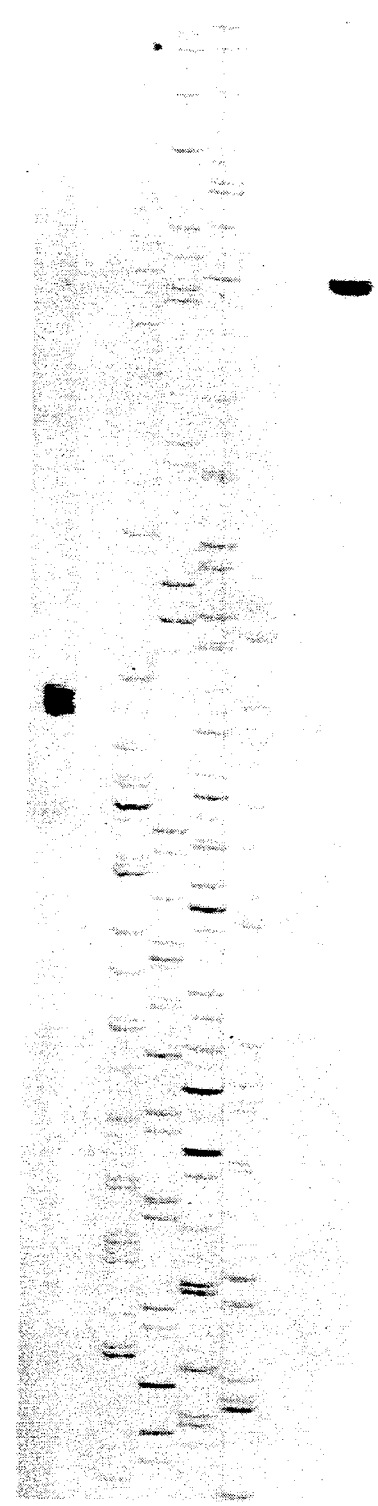
Figure 20:
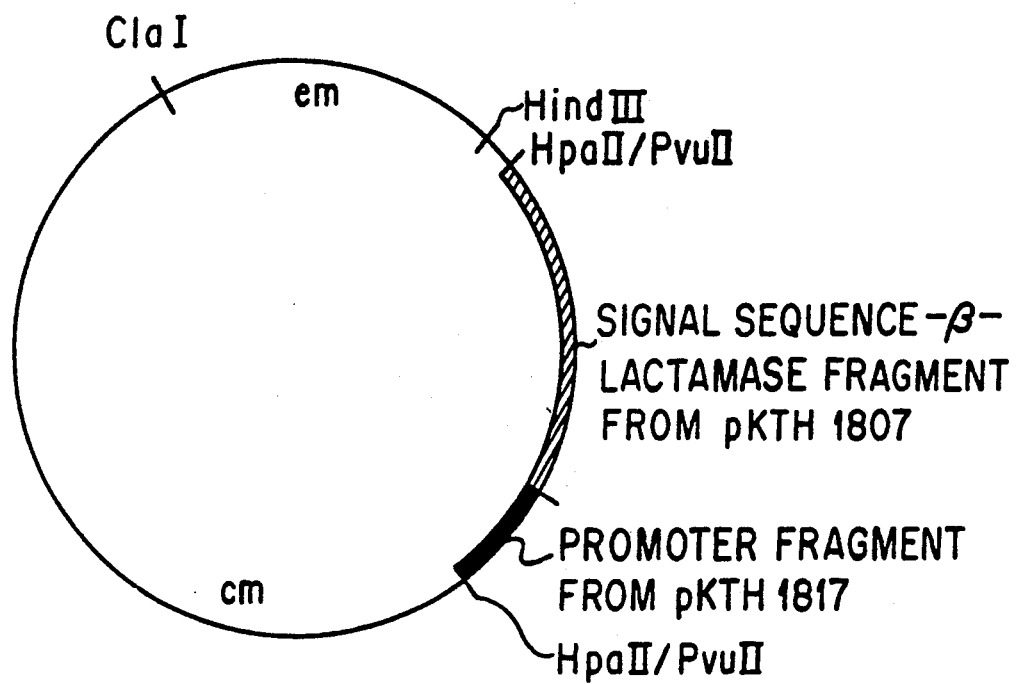
FIG. 20: Construction of hybrid vector pKTH1889.

Since heterogeneity among subclones was observed, four clones that retained both β-lactamase activity and DNA structure unchanged were selected for further transformations. The four secretion vectors were designated pKTH1805, pKTH1806, pKTH1807 and pKTH1809 (FIG. 7) respectively.

EXAMPLE VII

Expression and Secretion of β-lactamase in Gram-positive Hosts

To test the functioning of the isolated promoter/signal sequence fragments in Gram-positive bacteria, the four different constructions were transformed into *B. subtilis* BRB1, *L. lactis* GRS5, and *L. plantarum* NRLB192. The strains were then grown in liquid culture, under optimal conditions for each specific host.

Cell and supernatant fractions from 8-10 hour cultivations were subjected to Nitrocefin assay (Table 7).

TABLE 7

β-lactamase Activity in Gram-positive Hosts

| | β-lactamase Activity U/ml | | | | | |
|---|---|---|---|---|---|---|
| | *B. subtilis* | | *L. lactis* | | *L. plantarum* | |
| Construction | Sup | Cells | Sup | Cells | Sup | Cells |
| pKTH1805 | 2.6 | 1.3 | 5.8 | 0 | < | < |
| pKTH1806 | 17.1 | 24.6 | 75.2 | 2.5 | 229.0 | 4.2 |
| pKTH1807 | 2.6 | 8.2 | 245 | 1.7 | 10.5 | 1.1 |
| pKTH1809 | 1.6 | 6.3 | 72.6 | 57 | 5.3 | < |
| Control[1] | < | < | < | <[2] | < | < |

[1]Each host strain without a plasmid.
[2]Below detection limit.

EXAMPLE IX

Estimation of Promoter Strength

Promoter strength was initially estimated by comparing the promoter's ability to support host growth on antibiotic plates (cm plates for strains cloned by promoter probe vector; ap plates for strains cloned by promoter/signal sequence vector), its ability to produce high MIC, or its ability to synthesize large amounts of gene product (chloramphenicol acetyl transferase or β-lactamase).

Figure 3A:
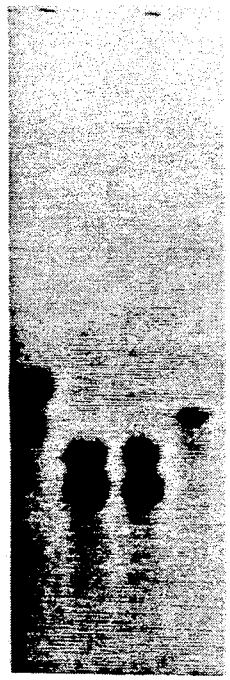
FIG. 3: mRNAs of *L. lactis* subsp. lactis promoter constructions (panel A) and promoter signal sequence constructions (panel B) obtained by Northern hybridization. Panel A: mRNAs were isolated from promoter constructions pKTH1816 (1), pKTH1817 (2), pKTH1820 (3), and pKTH1821 (4) and probed with labeled pPL603. To visualize the bands, X-ray film was exposed 1 h. Panel B: mRNAs were isolated from promoter signal sequence constructions pKTH1805 (5), pKTH1806 (6), pKTH1807 (7), and pKTH1809 (8), as a probe labeled pKTH78 was used. To visualize the bands, the film was exposed overnight.
Figure 3B:
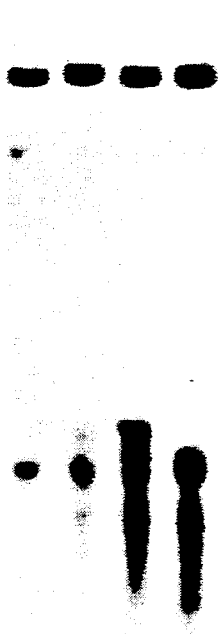

Selected clones (promoter clones pKTH1816, pKTH1817, pKTH1820 and pKTH1821) were further studied by Northern hybridization (FIG. 3). The results indicated that promoters cloned by promoter probe vector (pKTH1750) produced more test gene (cat) specific mRNA than did promoters cloned together with the signal sequence (the test gene in the latter case was bla). The difference was about 5-10 fold, when the differences between the specific activities of the probes were taken into account. Judged by transcriptional efficiency, the promoters cloned by the cat-plasmid pKTH1750 appeared stronger than promoters cloned together with the signal sequence.

EXAMPLE X

Construction of Hybrid Vectors

To demonstrate the manner in which the different promoters and signal sequences function together as hybrid expression units according to the present invention, the promoter on the expression/secretion plasmid pKTH1807 was replaced by the promoter on the expression plasmid pKTH1817.

The promoter was taken from plasmid pKTH1817 by the polymerase chain reaction (PCR) technique, using oligonucleotides A and B as primers (FIG. 18). Primer B for the 3'-end of the promoter fragment was designed so that, at the end of the PCR fragment, a restriction enzyme recognition site for XbaI was created.

The signal sequence-β-lactamase (bla) region was taken from plasmid pKTH1807 by PCR, using oligonucleotides C and D as primers. The 5'-end primer (primer C) was designed so that a restriction enzyme recognition site for XbaI was created.

Both the promoter fragment and the signal sequence-bla fragment obtained by PCR were digested with XbaI and purified on an agarose gel. They were ligated (as a 1:1 molar concentration ratio of signal sequence-bla to promoter fragment). The ligation of the XbaI site between the promoter and the signal sequence fragments regenerated the authentic 3'- and 5'- sequences at the joint region. The ligation mixture was digested with BglII and ClaI. The digestion mixture was run in an agarose gel, from which the proper fragment—containing the promoter ligated to the signal sequence bla—was isolated. This fragment was amplified with PCR and digested with PvuII. It was ligated to a pVS2-vector, which was digested with HpaII and made blunt by the Klenow enzyme.

TABLE 8

β-lactamase Activity of a Hybrid Construction

| | β-lactamase Activity (U/ml) | |
|---|---|---|
| Construction | sup | cells |
| pKTH1807 | 268 | 1.3 |
| pKTH1889 | 2,892 | 4.6 |

The ligation mixture was transformed into competent *E. coli* ERF173 cells and plated on Luria-ap (100 μg/ml) plates. Transformants so obtained were streaked several times on ap plates, in order to get stable cultures.

From the clones so obtained, the plasmid was isolated, transformed to *L. lactis* GRS5 cells, and plated on M17GS-cm (5 μg/ml) plates. From these transformations, a clone (pKTH1889) was obtained which, as shown in Table 8, produced approximately ten times more β-lactamase than *L. lactis* strain pKTH1807, which contained the original promoter/signal sequence combination.

What is claimed is:

1. A plasmid selected from the group consisting of plasmids pKTH1805, pKTH1806, pKTH1807 and pKTH1809.

2. The plasmid pKTH1889.

3. The plasmid of claim 2 further comprising a second nucleotide sequence encoding a protein or peptide which it is desired to express, wherein said second nucleotide sequence encoding said protein or peptide is operably linked in frame to the *L. lactis* supsp. lactis secretion sequence in said plasmid.

4. A plasmid comprising a *Lactococcus lactis* promoter-secretion signal sequence, wherein said *Lactococcus lactis* promoter-secretion signal sequence is selected from the *Lactococcus lactis* promoter-secretion signal sequence of plasmid pKTH1797, pKTH1798, pKTH1799, pKTH1801, pKTH1805, pKTH1806, pKTH1807 or pKTH1809.

5. A hybrid expression unit, comprising the *Lactococcus lactis* promoter sequence of any one of the plasmids selected from the group consisting of pKTH1789, pKTH1816, pKTH1817, pKTH1820, pKTH1821 and pKTH1874, operably linked in frame to the *Lactococcus lactis* secretion signal sequence of any one of the plasmids selected from the group consisting of pKTH1797, pKTH1798, pKTH1799, pKTH1801, pKTH1805, pKTH1806, pKTH1807 and pKTH1809.

6. The hybrid expression unit of claim 5, wherein said promoter sequence is derived from the plasmid pKTH1817, and wherein said secretion signal sequence is derived from the plasmid pKTH1807.

7. The hybrid expression unit of claims 5 or 6, further comprising a second nucleotide sequence encoding a protein or peptide which it is desired to express, wherein said second nucleotide sequence encoding said protein or peptide is operably linked in frame to the *L. lactis* subsp. lactis secretion sequence in said expression unit.

8. The plasmid of claim 1, further comprising a second nucleotide sequence encoding a protein or peptide which it is desired to express, wherein said second nucleotide sequence encoding said protein or peptide is operably linked in frame to the *L. lactis* subsp. lactis-derived secretion sequence in said plasmid.

9. The hybrid expression unit of claim 7, wherein said protein or peptide is heterologous to *Lactococcus lactis* subsp. lactis.

10. The hybrid expression unit of claim 7, wherein said protein or peptide is homologous to *Lactococcus lactis* subsp. lactis.

11. A Gram-positive host cell transformed with the hybrid expression unit of claim 7.

12. The host cell of claim 11, wherein said cell is selected from the group consisting of *B. subtilis*, Lactococci and Lactobacillus.

13. The host cell of claim 12, wherein said host is *Lactococcus lactis* subsp. lactis.

* * * * *

UNITED STATES PATENT AND TRADEMARK OFFICE
CERTIFICATE OF CORRECTION

Page 1 of 3

PATENT NO. : 5,242,821
DATED : September 7, 1993
INVENTOR(S) : Palva, et al

It is certified that error appears in the above-indentified patent and that said Letters Patent is hereby corrected as shown below:

On the title page: "Inventors", add --, Teija Koivula, Helsinki, Finland, Atte von Wright, Kuopio, Finland--

In column 1, in line 14, delete "plasmics" and substitute therefor --plasmids--

In column 2, in line 33, delete "a." and substitute therefor --al.--

In column 3, in line 37, delete "alayzed" and substitute therefor --analyzed--

In column 3, in line 47, delete "lactis" and substitute therefor --*lactis*--

In column 3, in line 53, delete "lactis" and substitute therefor --*lactis*--

In column 4, in line 27, delete "pKTH1798" and substitute therefor --pKTH1789--

In column 12, in line 25, delete "GenePulserTM" and substitute therefor --GenePulser™--

UNITED STATES PATENT AND TRADEMARK OFFICE
CERTIFICATE OF CORRECTION

PATENT NO. : 5,242,821

DATED : September 7, 1993

INVENTOR(S) : Palva, et al

It is certified that error appears in the above-indentified patent and that said Letters Patent is hereby corrected as shown below:

In column 13, in line 8, delete "6 1 mM MgCl$_2$" and substitute therefor -- 6 mM MgCl$_2$--

In column 13, in line 54, delete "antinomycin" and substitute therefor --actinomycin--

In column 13, in line 55, delete "deoxycytidial" and substitute therefor --deoxycytidine--

In column 15, in line 11, delete "ligated" and substitute therefor --ligation--

In column 15, in lines 25, 29 and 32, delete "CAT" and substitute therefor --*cat*--

In column 15, in line 40, delete "cat" and substitute therefor --*cat*--

In column 16, in lines 3, delete "CAT" and substitute therefor --*cat*--

In column 16, line 50, delete "pb" and substitute therefor --bp--

UNITED STATES PATENT AND TRADEMARK OFFICE
CERTIFICATE OF CORRECTION

PATENT NO. : 5,242,821
DATED : September 7, 1994
INVENTOR(S) : Palva, et al

It is certified that error appears in the above-indentified patent and that said Letters Patent is hereby corrected as shown below:

In column 17, line 4, delete "know" and substitute therefor --known--

In column 19, line 31, delete "EXAMPLE IX" and substitute therefor --EXAMPLE VIII--

In column 19, line 56, delete "EXAMPLE X" and substitute therefor --EXAMPLE IX--

In column 20, line 53, delete "supsp." and substitute therefor --subsp.--

In column 21, lines 4 and 6, delete "derived"

Signed and Sealed this

Fourth Day of October, 1994

Attest:

BRUCE LEHMAN

Attesting Officer     *Commissioner of Patents and Trademarks*